(12) United States Patent
Ramirez et al.

(10) Patent No.: US 9,427,397 B2
(45) Date of Patent: Aug. 30, 2016

(54) ROSACEA TREATMENTS AND KITS FOR PERFORMING THEM

(75) Inventors: José E. Ramirez, Key West, FL (US); Hovig Ounanian, Denton, TX (US)

(73) Assignee: Obagi Medical Products, Inc., Bridgewater, NJ (US)

( * ) Notice: Subject to any disclaimer, the term of this patent is extended or adjusted under 35 U.S.C. 154(b) by 0 days.

(21) Appl. No.: 13/368,915

(22) Filed: Feb. 8, 2012

(65) Prior Publication Data
US 2013/0039869 A1  Feb. 14, 2013

Related U.S. Application Data

(63) Continuation of application No. 13/144,833, filed as application No. PCT/US2010/021995 on Jan. 25, 2010.

(60) Provisional application No. 61/146,960, filed on Jan. 23, 2009, provisional application No. 61/225,041, filed on Jul. 13, 2009.

(51) Int. Cl.
| | | |
|---|---|---|
| *A61K 9/00* | (2006.01) | |
| *A61K 8/27* | (2006.01) | |
| *A61K 8/362* | (2006.01) | |
| *A61K 8/368* | (2006.01) | |
| *A61K 8/38* | (2006.01) | |
| *A61K 8/49* | (2006.01) | |
| *A61K 8/67* | (2006.01) | |
| *A61K 31/07* | (2006.01) | |
| *A61K 31/222* | (2006.01) | |
| *A61K 31/30* | (2006.01) | |
| *A61K 31/315* | (2006.01) | |
| *A61K 31/4168* | (2006.01) | |
| *A61K 31/59* | (2006.01) | |
| *A61Q 19/00* | (2006.01) | |
| *A61K 31/60* | (2006.01) | |
| *A61K 33/30* | (2006.01) | |
| *A61K 45/06* | (2006.01) | |

(52) U.S. Cl.
CPC .............. *A61K 9/0014* (2013.01); *A61K 8/27* (2013.01); *A61K 8/362* (2013.01); *A61K 8/368* (2013.01); *A61K 8/38* (2013.01); *A61K 8/4913* (2013.01); *A61K 8/67* (2013.01); *A61K 8/671* (2013.01); *A61K 31/07* (2013.01); *A61K 31/222* (2013.01); *A61K 31/30* (2013.01); *A61K 31/315* (2013.01); *A61K 31/4168* (2013.01); *A61K 31/59* (2013.01); *A61K 31/60* (2013.01); *A61K 33/30* (2013.01); *A61K 45/06* (2013.01); *A61Q 19/00* (2013.01); *A61K 2800/88* (2013.01)

(58) Field of Classification Search
CPC .. A61K 8/18; A61K 9/0014; A61K 31/4164; A61K 33/30; A61K 33/34; A61K 2800/596; A61K 45/06; A61K 31/59; A61K 31/60; A61K 8/67; A61K 8/671; A61K 31/07; A61K 31/222; A61K 31/30; A61K 31/315; A61K 31/4168; A61K 8/27; A61K 8/368; A61K 8/38; A61K 8/4913; A61K 2800/88; A61K 2800/595; A61Q 19/00; A61Q 19/005; Y10S 514/887; Y10S 514/93; Y10S 514/88
USPC ........... 424/78.05, 78.07, 401, 406, 489, 59, 424/60, 69; 514/183, 284, 398, 494, 506, 514/532, 546, 557, 561, 568, 579, 618, 514/714; 556/114
See application file for complete search history.

(56) References Cited

U.S. PATENT DOCUMENTS

| | | |
|---|---|---|
| 46,494 A | 2/1865 | Pike |
| 51,868 A | 1/1866 | Schuster |
| 55,889 A | 6/1866 | Noll |
| 81,008 A | 8/1868 | Roemheld |
| 81,711 A | 9/1868 | Van Wagenen |
| 87,343 A | 3/1869 | Johnson |
| 88,973 A | 4/1869 | McDowell |
| 92,065 A | 6/1869 | Lighthall |
| 93,300 A | 8/1869 | Hall et al. |
| 116,875 A | 7/1871 | Shannon |
| 124,751 A | 3/1872 | Lauer |
| 127,925 A | 6/1872 | Roskopf |

(Continued)

FOREIGN PATENT DOCUMENTS

| | | |
|---|---|---|
| EP | 2 087 880 | 8/2009 |
| JP | 2001039809 | 2/2001 |

(Continued)

OTHER PUBLICATIONS

ZenMed: "Rosacea treatment system from ZenMed", Jul. 29, 2008, Retrieved from the Internet: URL:<http://web.archive.org/web/20080729052452/zenmed.com/skincare/rosacea/> (Applicants have not supplied their date of download or retrieval from the Internet).*

(Continued)

*Primary Examiner* — Jane C Oswecki
(74) *Attorney, Agent, or Firm* — Kilpatrick Townsend & Stockton LLP

(57) ABSTRACT

Regimen for the treatment of rosacea include the application of an anti-redness composition to at least a portion of the cleansed area of skin afflicted with rosacea. The regimen may include the application of one or more of a polymetal complex, a composition containing metronidazole, and/or a protective composition. Kits containing components useful in performing such regimens are also described.

7 Claims, No Drawings

(56) References Cited

U.S. PATENT DOCUMENTS

| | | |
|---|---|---|
| 128,385 A | 6/1872 | Goffinet |
| 145,749 A | 6/1873 | Pawlewski et al. |
| 140,768 A | 7/1873 | Fisher |
| 143,133 A | 9/1873 | Fehr |
| 149,857 A | 1/1874 | Halpen |
| 173,607 A | 6/1875 | Fehr |
| 171,875 A | 1/1876 | Sievers |
| 209,331 A | 6/1878 | Littleton |
| 229,014 A | 6/1880 | Sharetts |
| 232,807 A | 10/1880 | Dennett |
| 238,015 A | 2/1881 | Yater |
| 264,783 A | 9/1882 | Squier |
| 277,221 A | 5/1883 | Buse |
| 284,335 A | 9/1883 | Scott |
| 318,468 A | 5/1885 | Haley |
| 320,836 A | 6/1885 | Bisaillon |
| 411,657 A | 9/1889 | Grosbety |
| 415,208 A | 11/1889 | Johson |
| 430,048 A | 6/1890 | Wainwright |
| 432,611 A | 7/1890 | Hall |
| 627,296 A | 6/1899 | Camnitzer |
| 928,539 A | 7/1909 | Pucciarelli |
| 944,738 A | 12/1909 | Loose |
| 992,937 A | 5/1911 | Brodbeck et al. |
| 1,059,841 A | 4/1913 | Crookes |
| 1,086,900 A | 2/1914 | David |
| 1,332,190 A | 2/1920 | Hull |
| 1,411,577 A | 4/1922 | Mullins et al. |
| 1,488,097 A | 3/1924 | Creger |
| 1,584,173 A | 5/1926 | Holzapfel |
| 1,593,485 A | 7/1926 | Crosnier |
| 1,627,963 A | 5/1927 | Fuller |
| 1,809,082 A | 6/1931 | Urkov et al. |
| 1,908,176 A | 5/1933 | Osterberg |
| 1,947,568 A | 2/1934 | Noonan |
| 1,949,797 A | 3/1934 | Kaufmann |
| 1,982,148 A | 11/1934 | Zimbron, Jr. |
| 2,002,829 A | 5/1935 | Osterberg |
| 2,054,989 A | 9/1936 | Moore |
| 2,087,162 A | 7/1937 | Moore |
| 2,095,092 A | 10/1937 | Barton |
| 2,114,490 A | 4/1938 | Harris |
| 2,129,836 A | 9/1938 | Goodman |
| 2,153,653 A | 4/1939 | Stux |
| 2,194,218 A | 3/1940 | Thurstan |
| 2,223,142 A | 11/1940 | Weirich |
| 2,241,331 A | 5/1941 | Shelton |
| 2,254,636 A | 9/1941 | Vangunten |
| 2,267,739 A | 12/1941 | Kemppe |
| 2,289,125 A | 7/1942 | Keil |
| 2,299,604 A | 10/1942 | Weirich |
| 2,344,830 A | 3/1944 | Mohs |
| 2,361,161 A | 10/1944 | Anderson |
| 2,370,561 A | 2/1945 | Mecca |
| 2,372,807 A | 4/1945 | Brown |
| 2,420,271 A | 5/1947 | Travis et al. |
| 2,420,389 A | 5/1947 | Travis et al. |
| 2,469,228 A | 5/1949 | Gertler |
| 2,527,686 A | 10/1950 | Sandberg |
| 2,556,567 A | 6/1951 | Wright |
| 2,602,039 A | 8/1952 | Wershaw |
| 2,649,398 A | 8/1953 | Wright et al. |
| 2,652,355 A | 9/1953 | Ercoli et al. |
| 2,673,364 A | 3/1954 | Diveley |
| 2,703,777 A | 3/1955 | Feinstein et al. |
| 2,736,681 A | 2/1956 | Tishler |
| 2,748,781 A | 6/1956 | Collat |
| 2,838,440 A | 6/1958 | Thurmon |
| 2,843,522 A | 7/1958 | Mahon |
| 2,846,322 A | 8/1958 | Buchalter |
| 2,870,150 A | 1/1959 | Wright et al. |
| 2,870,151 A | 1/1959 | Wright et al. |
| 2,872,372 A | 2/1959 | Hull |
| 2,991,224 A | 7/1961 | Bell |
| 3,013,883 A | 12/1961 | Welcker et al. |
| 3,033,755 A | 5/1962 | Jacobi |
| 3,035,988 A | 5/1962 | Cohen |
| 3,084,105 A | 4/1963 | Slodki |
| 3,137,622 A | 6/1964 | Mueller et al. |
| 3,146,168 A | 8/1964 | Battista |
| 3,164,523 A | 1/1965 | Fox et al. |
| 3,184,376 A | 5/1965 | Degoli |
| 3,210,248 A | 10/1965 | Feldmann et al. |
| 3,215,599 A | 11/1965 | Thau et al. |
| 3,255,079 A | 6/1966 | Schroeder et al. |
| 3,290,218 A | 12/1966 | de Jong |
| 3,317,372 A | 5/1967 | Hart |
| 3,366,114 A | 1/1968 | Kanter |
| 3,590,123 A | 6/1971 | Melloh et al. |
| 3,749,772 A | 7/1973 | Cardarelli et al. |
| 3,821,370 A | 6/1974 | Tenta |
| 3,821,371 A | 6/1974 | Battista |
| 3,826,845 A | 7/1974 | Suyama et al. |
| 3,856,941 A | 12/1974 | Turner |
| 3,896,238 A | 7/1975 | Smith |
| 3,903,268 A | 9/1975 | Balassa |
| 3,949,072 A | 4/1976 | Tenta |
| 4,048,300 A | 9/1977 | Tomlinson et al. |
| 4,054,596 A | 10/1977 | Koshar et al. |
| 4,062,937 A | 12/1977 | Rea |
| 4,100,269 A | 7/1978 | Pader |
| 4,129,510 A | 12/1978 | Smith |
| 4,138,477 A | 2/1979 | Gaffar |
| 4,146,607 A | 3/1979 | Ritchey |
| 4,154,911 A | 5/1979 | Bak et al. |
| 4,160,821 A | 7/1979 | Sipos |
| 4,161,526 A | 7/1979 | Gorman |
| 4,166,108 A | 8/1979 | Brown et al. |
| 4,226,851 A | 10/1980 | Sompayrac |
| 4,226,889 A | 10/1980 | Yuhas |
| 4,229,430 A | 10/1980 | Fahim et al. |
| 4,229,437 A | 10/1980 | Likens et al. |
| 4,255,418 A | 3/1981 | Bailey |
| 4,273,763 A | 6/1981 | Horrobin |
| 4,285,967 A | 8/1981 | Gubernick et al. |
| 4,291,025 A | 9/1981 | Pellico |
| 4,298,601 A | 11/1981 | Howard |
| 4,302,447 A | 11/1981 | Horrobin |
| 4,305,842 A | 12/1981 | Asakawa et al. |
| 4,309,989 A | 1/1982 | Fahim |
| 4,310,516 A | 1/1982 | Chang et al. |
| 4,315,916 A | 2/1982 | Likens et al. |
| 4,322,400 A | 3/1982 | Yuhas |
| 4,330,527 A | 5/1982 | Arima et al. |
| 4,331,653 A | 5/1982 | Brown et al. |
| 4,335,110 A | 6/1982 | Collins |
| 4,349,536 A | 9/1982 | Hausler |
| 4,372,296 A | 2/1983 | Fahim |
| 4,375,968 A | 3/1983 | Manhart |
| 4,376,115 A | 3/1983 | McCrorey |
| 4,395,398 A | 7/1983 | Yamamoto |
| 4,406,881 A | 9/1983 | Ladanyi |
| 4,428,933 A | 1/1984 | King |
| 4,430,324 A | 2/1984 | Viccaro |
| 4,444,755 A | 4/1984 | Horrobin |
| 4,465,666 A | 8/1984 | Lukas et al. |
| 4,469,684 A | 9/1984 | Huggins et al. |
| 4,477,439 A | 10/1984 | D'Alelio |
| 4,486,488 A | 12/1984 | Pietsch et al. |
| 4,503,037 A | 3/1985 | Szijjarto et al. |
| 4,512,978 A | 4/1985 | Inwood |
| 4,515,779 A | 5/1985 | Elliott |
| 4,522,806 A | 6/1985 | Muhlemann et al. |
| 4,568,540 A | 2/1986 | Asano et al. |
| 4,604,234 A | 8/1986 | Fujii et al. |
| 4,606,920 A | 8/1986 | Walter |
| 4,622,248 A | 11/1986 | Leach et al. |
| 4,647,452 A | 3/1987 | Ritchey et al. |
| 4,652,444 A | 3/1987 | Maurer |
| 4,654,213 A | 3/1987 | Ramirez et al. |
| 4,661,354 A | 4/1987 | Finnerty |
| 4,665,054 A | 5/1987 | Pickart |
| 4,678,664 A | 7/1987 | Schmolka |
| 4,683,133 A | 7/1987 | Southard |

(56) References Cited

U.S. PATENT DOCUMENTS

| | | |
|---|---|---|
| 4,708,864 A | 11/1987 | Maurer |
| 4,713,242 A | 12/1987 | Trenzeluk |
| 4,760,051 A | 7/1988 | Pickart |
| 4,762,715 A | 8/1988 | Lukas et al. |
| 4,767,753 A | 8/1988 | Pickart |
| 4,810,693 A | 3/1989 | Pickart |
| 4,816,254 A | 3/1989 | Moss |
| 4,830,716 A | 5/1989 | Ashmead |
| 4,847,083 A | 7/1989 | Clark |
| 4,849,211 A | 7/1989 | Schrauzer |
| 4,855,138 A | 8/1989 | Trenzeluk |
| 4,863,987 A | 9/1989 | Hoshino et al. |
| 4,874,361 A | 10/1989 | Obagi |
| 4,877,770 A | 10/1989 | Pickart |
| 4,895,727 A | 1/1990 | Allen |
| 4,911,932 A | 3/1990 | Clum et al. |
| 4,937,230 A | 6/1990 | Pickart |
| 4,938,969 A | 7/1990 | Schinitsky et al. |
| 4,956,354 A | 9/1990 | Gutierrez |
| RE33,512 E | 1/1991 | Ramirez et al. |
| 4,992,259 A | 2/1991 | Schiraldi et al. |
| 5,000,944 A | 3/1991 | Prencipe et al. |
| 5,023,237 A | 6/1991 | Pickart |
| 5,059,588 A | 10/1991 | Pickart |
| 5,075,019 A | 12/1991 | Evans et al. |
| 5,075,469 A | 12/1991 | Chevion |
| 5,079,010 A | 1/1992 | Natterer |
| 5,091,171 A | 2/1992 | Yu et al. |
| 5,091,193 A | 2/1992 | Enjolras et al. |
| 5,093,099 A | 3/1992 | Haishi et al. |
| 5,099,034 A | 3/1992 | Yoshida et al. |
| 5,104,644 A | 4/1992 | Douglas |
| 5,118,665 A | 6/1992 | Pickart |
| 5,120,831 A | 6/1992 | Pickart |
| 5,135,913 A | 8/1992 | Pickart |
| 5,145,838 A | 9/1992 | Pickart |
| 5,154,932 A | 10/1992 | Burba, III et al. |
| 5,164,367 A | 11/1992 | Pickart |
| 5,165,914 A | 11/1992 | Vlock |
| 5,166,176 A | 11/1992 | Obagi et al. |
| 5,174,990 A | 12/1992 | Douglas |
| 5,177,061 A | 1/1993 | Pickart |
| 5,209,932 A | 5/1993 | Nichols |
| 5,214,032 A | 5/1993 | Pickart |
| 5,227,156 A | 7/1993 | Wiese |
| 5,232,691 A | 8/1993 | Lemole |
| 5,240,696 A | 8/1993 | Van Der Ouderaa et al. |
| 5,244,651 A | 9/1993 | Kayane et al. |
| 5,258,183 A | 11/1993 | Grimberg |
| 5,310,546 A | 5/1994 | Douglas |
| 5,330,748 A | 7/1994 | Winston et al. |
| 5,330,749 A | 7/1994 | Giacin et al. |
| 5,348,943 A | 9/1994 | Pickart |
| 5,352,438 A | 10/1994 | N'Guyen et al. |
| 5,382,431 A | 1/1995 | Pickart |
| 5,385,727 A | 1/1995 | Winston et al. |
| 5,401,730 A | 3/1995 | Sauvage et al. |
| 5,424,077 A | 6/1995 | Lajoie |
| 5,439,863 A | 8/1995 | Bottcher et al. |
| 5,455,023 A | 10/1995 | Giacin et al. |
| 5,466,470 A | 11/1995 | Lajoie |
| 5,480,975 A | 1/1996 | Goldberg et al. |
| 5,482,720 A | 1/1996 | Murphy et al. |
| 5,484,597 A | 1/1996 | Slavtcheff et al. |
| 5,496,539 A | 3/1996 | Mobley et al. |
| 5,500,448 A | 3/1996 | Cummins et al. |
| 5,504,055 A | 4/1996 | Hsu |
| 5,547,676 A | 8/1996 | Rocher et al. |
| 5,550,183 A | 8/1996 | Pickart |
| 5,552,147 A | 9/1996 | Znaiden et al. |
| 5,554,375 A | 9/1996 | Pickart |
| 5,554,647 A | 9/1996 | Perricone |
| 5,582,817 A | 12/1996 | Otsu et al. |
| 5,597,550 A | 1/1997 | Mo |
| 5,597,552 A | 1/1997 | Herms et al. |
| 5,616,313 A | 4/1997 | Williams et al. |
| 5,622,724 A | 4/1997 | Bryce-Smith |
| 5,624,675 A | 4/1997 | Kelly |
| 5,631,013 A | 5/1997 | Bergmann et al. |
| 5,632,972 A | 5/1997 | Williams et al. |
| 5,645,840 A | 7/1997 | Lajoie et al. |
| 5,663,213 A | 9/1997 | Jones et al. |
| 5,686,083 A | 11/1997 | Chamness |
| 5,688,492 A | 11/1997 | Galley et al. |
| 5,690,967 A | 11/1997 | Yu et al. |
| 5,696,169 A | 12/1997 | Otsu et al. |
| 5,698,184 A | 12/1997 | Pickart |
| 5,707,609 A | 1/1998 | Mo |
| 5,708,023 A | 1/1998 | Modak et al. |
| 5,728,404 A | 3/1998 | Von Rheinbaben et al. |
| 5,747,005 A | 5/1998 | Barels et al. |
| 5,753,637 A | 5/1998 | Fried |
| 5,762,945 A | 6/1998 | Ashley et al. |
| 5,780,020 A | 7/1998 | Peterson et al. |
| 5,795,574 A | 8/1998 | Breton et al. |
| 5,798,121 A | 8/1998 | Cauwet et al. |
| 5,827,884 A | 10/1998 | Obagi et al. |
| 5,837,270 A | 11/1998 | Burgess |
| 5,855,873 A | 1/1999 | Yam |
| 5,858,335 A | 1/1999 | Lucas et al. |
| 5,858,371 A | 1/1999 | Singh et al. |
| 5,858,993 A | 1/1999 | Pickart |
| 5,861,143 A | 1/1999 | Peterson et al. |
| 5,861,144 A | 1/1999 | Peterson et al. |
| 5,861,145 A | 1/1999 | Lucas et al. |
| 5,861,146 A | 1/1999 | Peterson et al. |
| 5,861,147 A | 1/1999 | Dodd et al. |
| 5,871,718 A | 2/1999 | Lucas et al. |
| 5,871,719 A | 2/1999 | Lucas et al. |
| 5,874,067 A | 2/1999 | Lucas et al. |
| 5,874,070 A | 2/1999 | Trinh et al. |
| 5,879,666 A | 3/1999 | Lucas et al. |
| 5,882,638 A | 3/1999 | Dodd et al. |
| 5,886,184 A | 3/1999 | Dolling et al. |
| 5,888,515 A | 3/1999 | Albert et al. |
| 5,888,522 A | 3/1999 | Pickart |
| 5,897,854 A | 4/1999 | Lucas et al. |
| 5,897,855 A | 4/1999 | Trinh et al. |
| 5,897,856 A | 4/1999 | Trinh et al. |
| 5,904,921 A | 5/1999 | Bresson-Rival et al. |
| 5,911,976 A | 6/1999 | Trinh et al. |
| 5,928,631 A | 7/1999 | Lucas et al. |
| 5,928,658 A | 7/1999 | Kishida et al. |
| 5,928,659 A | 7/1999 | Moy |
| 5,935,608 A | 8/1999 | Fujikawa et al. |
| 5,942,214 A | 8/1999 | Lucas et al. |
| 5,948,390 A | 9/1999 | Nelson et al. |
| 5,951,990 A | 9/1999 | Ptchelintsev |
| 5,955,067 A | 9/1999 | Oge et al. |
| 5,961,993 A | 10/1999 | Boussouira et al. |
| 5,965,137 A | 10/1999 | Petrus |
| 5,965,610 A | 10/1999 | Modak et al. |
| 5,972,999 A | 10/1999 | Murad |
| 5,980,477 A | 11/1999 | Kelly |
| 5,994,403 A | 11/1999 | Donatiello |
| 5,997,600 A | 12/1999 | Dean |
| 6,019,976 A | 2/2000 | Bryant |
| 6,022,565 A | 2/2000 | Albert et al. |
| 6,030,605 A | 2/2000 | D'Ameila et al. |
| 6,037,386 A | 3/2000 | Modak et al. |
| 6,046,178 A | 4/2000 | Silvetti, Sr. |
| 6,060,079 A | 5/2000 | Freeman et al. |
| 6,071,543 A | 6/2000 | Thornfeldt |
| 6,083,490 A | 7/2000 | Ellis et al. |
| 6,086,666 A | 7/2000 | Noguchi et al. |
| 6,103,247 A | 8/2000 | Boussouira et al. |
| 6,103,273 A | 8/2000 | Antoun |
| 6,113,636 A | 9/2000 | Ogle |
| 6,121,254 A | 9/2000 | Saint-Leger |
| 6,123,925 A | 9/2000 | Barry et al. |
| 6,132,743 A | 10/2000 | Kuroda et al. |
| 6,143,318 A | 11/2000 | Gilchrist et al. |
| 6,149,947 A | 11/2000 | Hon et al. |
| 6,183,785 B1 | 2/2001 | Westfall |

(56) References Cited

U.S. PATENT DOCUMENTS

| | | |
|---|---|---|
| 6,190,407 B1 | 2/2001 | Ogle et al. |
| 6,191,167 B1 | 2/2001 | Yu et al. |
| 6,197,815 B1 | 3/2001 | Hsu |
| 6,200,580 B1 | 3/2001 | Horino et al. |
| 6,200,680 B1 | 3/2001 | Takeda et al. |
| 6,217,914 B1 | 4/2001 | Meisner |
| 6,221,403 B1 | 4/2001 | Nesbit |
| 6,224,896 B1 | 5/2001 | Redmond |
| 6,248,370 B1 | 6/2001 | Harris |
| 6,261,574 B1 | 7/2001 | Costello |
| 6,267,782 B1 | 7/2001 | Ogle et al. |
| 6,287,541 B1 | 9/2001 | Creeth et al. |
| 6,303,651 B1 | 10/2001 | Hersh |
| 6,322,588 B1 | 11/2001 | Ogle et al. |
| 6,322,820 B1 | 11/2001 | Simoneau |
| 6,331,567 B1 | 12/2001 | Watson et al. |
| 6,361,800 B1 | 3/2002 | Cooper et al. |
| 6,375,942 B1 | 4/2002 | Rico |
| 6,395,301 B1 | 5/2002 | Cantin |
| 6,416,744 B1 | 7/2002 | Robinson et al. |
| 6,426,424 B1 | 7/2002 | Ashmead et al. |
| 6,444,699 B2 | 9/2002 | Meisner |
| 6,451,294 B1 | 9/2002 | Simon |
| 6,471,972 B1 | 10/2002 | Bonte et al. |
| 6,475,526 B1 | 11/2002 | Smith |
| 6,517,849 B1 | 2/2003 | Seger et al. |
| 6,518,240 B1 | 2/2003 | Pedersen et al. |
| 6,521,265 B1 | 2/2003 | Patterson |
| 6,558,710 B1 | 5/2003 | Godfrey |
| 6,579,541 B2 | 6/2003 | Antelman |
| 6,582,684 B1 | 6/2003 | Abrahamson |
| 6,582,710 B2 | 6/2003 | Deckers et al. |
| 6,592,852 B1 | 7/2003 | Ryles et al. |
| 6,599,513 B2 | 7/2003 | Deckers et al. |
| 6,607,711 B2 | 8/2003 | Pedersen |
| 6,607,716 B1 | 8/2003 | Smith et al. |
| 6,627,178 B1 | 9/2003 | Cawthon |
| 6,660,306 B2 | 12/2003 | Peshoff |
| 6,663,852 B2 | 12/2003 | Simon |
| 6,680,073 B1 | 1/2004 | Tarbet |
| 6,682,720 B2 | 1/2004 | Ryles et al. |
| 6,696,071 B2 | 2/2004 | Kelly |
| 6,710,079 B1 | 3/2004 | Ashmead et al. |
| 6,726,919 B2 | 4/2004 | Pace et al. |
| 6,730,309 B2 | 5/2004 | Horino |
| 6,730,329 B1 | 5/2004 | Smith |
| 6,743,416 B2 | 6/2004 | Riedl |
| 6,750,209 B1 | 6/2004 | Hudson et al. |
| 6,773,698 B1 | 8/2004 | Melinte et al. |
| 6,780,439 B2 | 8/2004 | Wilk |
| 6,800,301 B2 | 10/2004 | Smith |
| 6,833,362 B2 | 12/2004 | Bowen, Jr. et al. |
| 6,844,012 B1 | 1/2005 | Forceville et al. |
| 6,849,277 B2 | 2/2005 | Roig |
| 6,855,341 B2 | 2/2005 | Smith |
| 6,858,201 B2 | 2/2005 | Pickart |
| 6,929,800 B2 | 8/2005 | Salman |
| 6,932,976 B2 | 8/2005 | Brooks |
| 6,939,568 B2 | 9/2005 | Burrell et al. |
| 6,942,878 B2 | 9/2005 | Ishii et al. |
| 6,949,248 B2 | 9/2005 | Nishihama |
| 6,949,249 B2 | 9/2005 | Healy et al. |
| 6,964,782 B1 | 11/2005 | Smith et al. |
| 6,979,468 B2 | 12/2005 | Pollard |
| 6,989,156 B2 | 1/2006 | Gillis |
| 6,992,203 B2 | 1/2006 | Trusovs |
| 7,008,647 B2 | 3/2006 | Burrell et al. |
| 7,014,870 B2 | 3/2006 | Hon et al. |
| 7,022,351 B2 | 4/2006 | Abdel-Monem et al. |
| 7,026,308 B1 | 4/2006 | Gavin et al. |
| 7,049,339 B2 | 5/2006 | Thomson |
| 7,060,729 B2 | 6/2006 | Babapour |
| 7,129,375 B2 | 10/2006 | Abdel-Monem et al. |
| 7,141,689 B2 | 11/2006 | Abdel-Monem et al. |
| 7,220,426 B2 | 5/2007 | Abdel-Monem et al. |
| 7,258,875 B2 * | 8/2007 | Chiou ............... A61K 31/555 424/641 |
| 7,687,650 B2 * | 3/2010 | Ramirez ............ C07F 3/003 556/114 |
| 7,897,800 B2 * | 3/2011 | Ramirez ............ C07C 55/02 556/114 |
| 7,927,614 B2 | 4/2011 | Faryniarz et al. |
| 8,303,984 B2 * | 11/2012 | Dorogi ............... A61K 8/19 424/450 |
| 8,557,817 B2 * | 10/2013 | DeJovin ............. A61K 31/137 514/249 |
| 2001/0014356 A1 | 8/2001 | Yoshida et al. |
| 2001/0041193 A1 | 11/2001 | Meisner |
| 2002/0001629 A1 | 1/2002 | Voellmy |
| 2002/0031557 A1 | 3/2002 | Meisner |
| 2002/0114847 A1 | 8/2002 | Peshoff |
| 2002/0182244 A1 | 12/2002 | Jackson |
| 2003/0004564 A1 | 1/2003 | Elkins et al. |
| 2003/0026848 A1 | 2/2003 | Joshi |
| 2003/0035825 A1 | 2/2003 | Shiau et al. |
| 2003/0059484 A1 | 3/2003 | Bonte et al. |
| 2003/0068351 A1 | 4/2003 | Roig |
| 2003/0069369 A1 | 4/2003 | Belenkaya et al. |
| 2003/0072819 A1 | 4/2003 | Tao |
| 2003/0077304 A1 | 4/2003 | McCadden |
| 2003/0077332 A1 | 4/2003 | Godfrey |
| 2003/0082219 A1 | 5/2003 | Warren et al. |
| 2003/0082223 A1 | 5/2003 | Healy et al. |
| 2003/0099721 A1 | 5/2003 | Yoshida et al. |
| 2003/0118623 A1 | 6/2003 | De Paoli Ambrosi |
| 2003/0133991 A1 | 7/2003 | Monroe et al. |
| 2003/0138497 A1 | 7/2003 | Sakuma et al. |
| 2003/0161892 A1 | 8/2003 | McFarland |
| 2003/0166510 A1 | 9/2003 | Pickart |
| 2003/0190371 A1 | 10/2003 | Graaf et al. |
| 2003/0194446 A1 | 10/2003 | Akes et al. |
| 2003/0199488 A1 | 10/2003 | Trotta |
| 2003/0215412 A1 | 11/2003 | Waugh et al. |
| 2003/0215522 A1 | 11/2003 | Johnson et al. |
| 2003/0224023 A1 | 12/2003 | Faryniarz et al. |
| 2003/0224027 A1 | 12/2003 | Faryniarz et al. |
| 2004/0022863 A1 | 2/2004 | Hamtini |
| 2004/0028708 A1 | 2/2004 | Brooks |
| 2004/0033270 A1 | 2/2004 | Kropf et al. |
| 2004/0037910 A1 | 2/2004 | Hon et al. |
| 2004/0057972 A2 * | 3/2004 | Shacknai ............ A61K 8/23 424/401 |
| 2004/0057973 A1 * | 3/2004 | Wittkowski ........ A61K 8/8111 424/401 |
| 2004/0058011 A1 | 3/2004 | Petersson |
| 2004/0058015 A1 | 3/2004 | Tao |
| 2004/0062730 A1 | 4/2004 | Kurosawa et al. |
| 2004/0062817 A1 | 4/2004 | Peshoff |
| 2004/0076686 A1 | 4/2004 | Riesinger |
| 2004/0091551 A1 | 5/2004 | Damji |
| 2004/0101541 A1 | 5/2004 | Heffernan et al. |
| 2004/0109902 A1 | 6/2004 | McDonagh et al. |
| 2004/0131700 A1 | 7/2004 | Cifra et al. |
| 2004/0147189 A1 | 7/2004 | Smith et al. |
| 2004/0156875 A1 | 8/2004 | Fabre et al. |
| 2004/0157921 A1 | 8/2004 | Cifra et al. |
| 2004/0170701 A1 | 9/2004 | Carter |
| 2004/0170703 A1 | 9/2004 | Hoekstra et al. |
| 2004/0170712 A1 | 9/2004 | Sadek El Mogy |
| 2004/0175433 A1 | 9/2004 | Thomson |
| 2004/0185015 A1 | 9/2004 | Zhang et al. |
| 2004/0185074 A1 | 9/2004 | Faryniarz et al. |
| 2004/0202689 A1 | 10/2004 | Subramanyan et al. |
| 2004/0220100 A1 | 11/2004 | Waugh et al. |
| 2004/0253321 A1 | 12/2004 | Fechner et al. |
| 2004/0258769 A1 | 12/2004 | Barker et al. |
| 2005/0032751 A1 | 2/2005 | Wang et al. |
| 2005/0048010 A1 | 3/2005 | Klis et al. |
| 2005/0069506 A1 | 3/2005 | Katusic et al. |
| 2005/0069588 A1 | 3/2005 | Taal |
| 2005/0074425 A1 | 4/2005 | Waugh et al. |
| 2005/0079229 A1 | 4/2005 | Cawthon |
| 2005/0100571 A1 | 5/2005 | Keyes |
| 2005/0123620 A1 | 6/2005 | Chiou |

(56) References Cited

U.S. PATENT DOCUMENTS

| | | |
|---|---|---|
| 2005/0136129 A1 | 6/2005 | Verheul-Koot et al. |
| 2005/0165079 A1 | 7/2005 | Shanler et al. |
| 2005/0175719 A1 | 8/2005 | Sun et al. |
| 2005/0202054 A1 | 9/2005 | Faryniarz et al. |
| 2005/0234239 A1 | 10/2005 | Taillefer et al. |
| 2005/0238730 A1 | 10/2005 | Le Fur et al. |
| 2006/0024339 A1 | 2/2006 | Murad |
| 2006/0029682 A1 | 2/2006 | Monroe et al. |
| 2006/0036007 A1 | 2/2006 | Hsieh et al. |
| 2006/0089407 A1 | 4/2006 | Maurer |
| 2007/0032751 A1 | 2/2007 | Roman |
| 2007/0163465 A1 | 7/2007 | Anderson et al. |
| 2007/0184017 A1 | 8/2007 | Faryniarz et al. |
| 2007/0190190 A1 | 8/2007 | Ramirez et al. |
| 2007/0191620 A1 | 8/2007 | Ramirez et al. |
| 2007/0203354 A1 | 8/2007 | Ramirez et al. |
| 2007/0238772 A1* | 10/2007 | Dolfi .................. A61K 45/06 514/398 |
| 2008/0081077 A1 | 4/2008 | Faryniarz et al. |
| 2008/0194664 A1* | 8/2008 | Kaoukhov ........... A61K 8/4946 514/398 |
| 2010/0247628 A1* | 9/2010 | Dorogi ................. A61K 8/19 424/450 |

FOREIGN PATENT DOCUMENTS

| | | | |
|---|---|---|---|
| WO | WO 94/15216 | 7/1994 | |
| WO | WO 02/100383 | 12/2002 | |
| WO | WO 2004/039238 A2 | 5/2004 | |
| WO | WO 2006/055526 | 5/2006 | |
| WO | WO 2006/131653 | 12/2006 | |
| WO | WO 2007/089267 | 8/2007 | |
| WO | WO2007/089267 A1 * | 8/2007 | ............ A61K 33/34 |
| WO | WO2010/085753 A1 * | 7/2010 | ............ A61K 45/00 |

OTHER PUBLICATIONS

Clinique: "Redness Solutions Redness Regime", Apr. 3, 2008; Retrieved from the Internet: URL<http://web.archive.org/web/20080403232732/http://www.clinique.co.uk/templates/products/sp_nonshaded.tmpl?> (Applicants have not supplied their date of download or retrieval from the Internet).*

ZenMed: "Rosacea treatment system from ZenMed", Jul. 29, 2008; Retrieved from the Internet: URL: <http://web.archive.org/web/20080729052452/zenmed.com/skincare/rosacea/> Note: Applicants have not supplied their date of download or retrieval from the Internet for this document.*

Clinique: "Redness Solutions Redness Regime", Apr. 3, 2008; Retrieved from the Internet: URL<http://web.archive.org/web/20080403232732/http://www.clinique.co.uk/templates/products/sp_nonshaded.tmpl?> /> Note: Applicants have not supplied their date of download or retrieval from the Internet for this document.*

Sephora: "Clinique Redness Solutions Kit", no publication date provided by Sephora, [Retrieved Sep. 2, 2013]; Retrieved from the Internet: URL< http://www.sephora.com/redness-solutions-kit-P209119.*

Clinique: "Redness Solutions Redness Regime", Apr. 3, 2008; Retrieved from the Internet: URL:<http://web.archive.org/web/20080403232732/http://www.clinique.co.uk/templates/products/sp_nonshaded.tmpl?> Note: Applicants have not supplied a date of their download or retrieval from the Internet for this document.*

Sephora: "Clinique Redness Solutions Kit"; no publication date provided by Sephora, [Retrieved Sep. 2, 2013]; Retrieved from the Internet: URL<http://www.sephora.com/redness-solutions-kit-P209119.*

Clinique: "Redness Solutions Redness Regime", Apr. 3, 2008; Retrieved from the Internet: URL<http://web.archive.org/web/20080403232732/http://www.clinique.co.uk/templates/plroducts/sp_nonshaded.tmpl?> Note: Applicants have not supplied a date of their download or retrieval from the Internet for this document.*

Sephora: "Clinique Redness Solutions Kit"; no publication date provided by Sephora; [Retrieved Sep. 2, 2013]; Retrieved from the Internet: URL<http://www.sephora.com/redness-solutions-kit-P209119>.*

Clinique: "Redness Solutions Redness Regime"; Apr. 3, 2008; Retrieved from the Internet: URL<http://www.web.archive.org/web/20080403232732/http://www.clinique.co.uk/templates/products/sp_nonshaded.tmpl?> Note: Applicants have not supplied a date of their download or retrieval from the Internet for this document.*

David Pascoe, Clinique Redness Solutions Ingredients; Jan. 24, 2008; [Retrieved Aug. 31, 2015], Retrieved from the Internet: URL<http://rosacea-support.org/clinique-redness-solutions-ingredients.html>.*

Rodríguez-Martín Y., "Alternating cationic-anionic layers in the [MII($H_2O$)$_6$][$Cu^{II}$(mal)$_2$($H_2O$)] complexes linked through hydrogen bonds (M = Mn, Co, Ni, Cu and Zn; $H_2$mal = Malonic acid)", CrystEngComm, 2002, vol. 4, No. 107, 631.

Hernández-Molina M., "A phase transition in the novel three-dimensional compound [$Eu_2$(mal)$_2$($H_2O$)$_6$] ($H_2$mal = malonic acid)", J.Chem.Soc., Dalton Trans. 2002, vol. 18, 3462.

Rodríguez-Martín, Y., "Structural Versatility of the Malonate Ligand as a Tool for Crystal Engineering in the Design of Molecular Magnets", Cryst. Eng. Comm. 2002, vol. 4, No. 87, 522-535.

Rodríguez-Martín, Y., "Combining coordination chemistry and hydrogen bonds: Synthesis, Crystal Structures and thermal behaviour of the complexes [MII(L)(bpy)($H_2O$)$_n$]•($NO_3$)$_2$ ($M^{II}$=Cu and Ni, n =1 or 2, L = malonamide, bipy = 2,2'-bipyridine)", J. Coord. Chem. (2002) in press.

Sanchiz, J., "Ferromagnetic coupling in the malonato-bridged copper(II) chains {[Cu(Im)$_2$(mal)]}$_n$ and {[Cu(2-Melm)$_2$(mal)]}$_n$ ($H_2$mal = Malonic Acid, Im = imidazole and 2-Melm = 2-methylimidazole)", New J. Chem. 2002, vol. 26, 1624.

Ruiz-Pérez, C., "Dimensionally controlled hydrogen-bonded nanostructures: Synthesis, structure, thermal and magnetic behaviour of the tris-(chelated)nickel(II) complex [Ni(bipy)$_3$]$Cl_2$.5.5$H_2O$ (bipy = 2,2'-bipyridine)", Inorg. Chim. Acta. 2002, vol. 336, 131-136.

Rodríguez-Martín, Y., "Extended network via hydrogen bond linkages of coordination compounds: Synthesis, crystal structure and thermal behavior of the complexes [MII(L)$_2$($NO_3$)$_2$] (MII =Cu, Co) and [Ni(L)$_2$($H_2O$)$_2$]•($NO_3$)$_2$ (L = malonamide)", Inorganica Chimica Acta . vol. 328, 169-178 (2002).

Rodríguez-Martín, Y., "Synthesis, crystal structure and magnetic properties of [Cu(bpym)(mal)($H_2O$)]•6$H_2O$ and [$Cu_2$(bpym)(mal)$_2$($H_2O$)$_2$]•4$H_2O$ (bpym = 2,2'-bipyrimidine, H2mal = Malonic Acid)", Inorganica Chimica Acta. vol. 326, 20-26 (2001).

Naumov, P., et al., "The Crystal Structure of Copper (II) Malonate Trihydrate", CCACAA, vol. 75, No. 3, 701-711 (2002).

Chen et al., "Preparation and Kinetics of the Thermal Decomposition of Nanosized $CuC_2O_4$-$ZnC_2O_4$ 2$H_2O$", Wuhan University Journal of Natural Sciences, vol. 11, No. 3, pp. 667-671, May 2006.

M.A. Gabal, "Kinetics of the Thermal Decomposition of $CuC_2O_4$-$ZnC_2O_4$ Mixture in Air", Thermochimica Acta 402 (2003) pp. 199-208.

Huang Lianrong et al., "Thermal Behavior of Kinetics ofthe Decomposition of $CuC_2O_4$•$ZnC_2O_4$ 2$H_2O$ by Different Preparation Methods", Journal of South-Central University for Nationalities (Nat. Sci. Edition), vol. 23, No. 3, pp. 12-16, Sep. 2004.

Ruiz-Pérez, et al.. "Malonic Acid: a multi-modal bridging ligand for new architectures and properties on molecule-based magnets" Polyhedron 2003, accepted.

Pasán, J., et al., "Malonate-based copper(II) coordination compounds: Ferromagnetic coupling controlled by dicarboxylates", Polyhedron 2003, accepted.

Rodríguez-Martín Y., "Alternating cationic-anionic layers in the [MII($H_2O$)$_6$][$Cu^{II}$(mal)$_2$($H_2O$)] complexes linked through hydrogen bonds (M=Mn, Co, Ni, Cu and Zn; $H_2$mal=Malonic acid)", CrystEngComm, 2002, vol. 4, No. 107, 631.

Hernández-Molina M., "A phase transition in the novel three-dimensional compound [$Eu_2$(mal)$_2$($H_2O$)$_6$]($H_2$mal=malonic acid)", J.Chem.Soc., Dalton Trans. 2002, vol. 18, 3462.

(56) References Cited

OTHER PUBLICATIONS

RodrlGuez-Martín, Y., "Structural Versatility of the Malonate Ligand as a Tool for Crystal Engineering in the Design of Molecular Magnets", *Cryst. Eng. Comm.* 2002, vol. 4, No. 87, 522-535.

Rodríguez-Martín, Y., "Combining coordination chemistry and hydrogen bonds: Synthesis, Crystal Structures and thermal behaviour of the complexes [MII(L)(bpy)(H$_2$O)$_n$]•(NO$_3$)$_2$ ($M^{II}$=Cu and Ni, n=1 or 2, L=malonamide, bipy=2,2'-bipyridine)", *J. Coord. Chem.* (2002) in press.

Sanchiz, J., "Ferromagnetic coupling in the malonato-bridged copper(II) chains {[Cu(Im)$_2$(mal)]}$_n$ and {[Cu(2-Melm)$_2$(mal)]}$_n$ (H$_2$mal=Malonic Acid, Im=imidazole and 2-Melm=2-methylimidazole)", *New J. Chem.* 2002, vol. 26, 1624.

Rodríguez-Martín, Y., "The flexibility of molecular components as a suitable tool in designing extended magnetic systems", *Cryst. Eng. Comm.* 2002, vol. 4, No. 73, 440-446.

Ruiz-Pérez, C., "Dimensionally controlled hydrogen-bonded nanostructures: Synthesis, structure, thermal and magnetic behaviour of the tris-(chelated)nickel(II) complex [Ni(bipy)$_3$]Cl$_2$.5. 5H$_2$O (bipy=2,2'-bipyridine)", *Inorg. Chico. Acta.* 2002, vol. 336, 131-136.

Rodríguez-Martín, Y., "Extended network via hydrogen bond linkages of coordination compounds: Synthesis, crystal structure and thermal behavior of the complexes [MII(L)$_2$(NO$_3$)$_2$] (MII=Cu, Co) and [Ni(L)$_2$(H$_2$O)$_2$]•(NO$_3$)$_2$ (L=malonamide)", *Inorganica Chimica Acta.* vol. 328, 169-178 (2002).

Rodríguez-Martín, Y., "Synthesis, crystal structure and magnetic properties of [Cu(bpym)(mal)(H$_2$O)]•6H$_2$O and [Cu$_2$(bpym)(mal)$_2$(H$_2$O)$_2$]•4H$_2$O (bpym=2,2'-bipyrimidine, H2mal=Malonic Acid)", *Inorganica Chimica Acta.* vol. 326, 20-26 (2001).

Delgado, F., "Alkali-Templated Malonate Copper (II) Complexes", *Acta Cryst.* A61, C358 (2005).

Naumov, P, et al., "The Crystal Structure of Copper (II) Malonate Trihydrate", *CCACCA*, vol. 75, No. 3, 701-711 (2002).

Filippova I.G., "Polymorphism of Coordination Compounds with Malonic Añid", *Moldavian Journal of the Physical Sciences*, 1vol. 1, No. 3, 87-93 (2002).

Tinker, D. et al., "Role of Selected Nutrients in Synthesis, Accumulation, and Chemical Modification of Connective Tissue Proteins", *Physiolgical Reviews*, vol. 65, No. 3, 607-657 (1985).

Philip, B., et al., "Dietary Zinc & Levels of Collagen, Elastin & Carbohydrate Components of Glycoproteins of Aorta, Skin & Cartilage in Rats", *Indian J. Exp. Biol.*, vol. 16, 370-372 (1978).

Homsy, R. et al., "Characterization of Human Skin Fibroblasts Elastase Activity", J. Invest. Dermatol, vol. 91, 472-477 (1988).

Chen et al., "Preparation and Kinetics of the Thermal Decomposition of Nanosized CuC$_2$O$_4$—ZnC$_2$O$_4$2H$_2$O", Wuhan University Journal of Natural Sciences, vol. 11, No. 3, pp. 667-671, May 2006.

M.A. Gabal, "Kinetics of the Thermal Decomposition of CuC$_2$O$_4$—ZnC$_2$O$_4$ Mixture in Air", Thermochimica Acta 402 (2003) pp. 199-208.

Huang Lianrong et al., "Thermal Behavior of Kinetics ofthe Decomposition of CuC$_2$O$_4$—ZnC$_2$O$_4$2H$_2$O by Different Preparation Methods", Journal of South-Central University for Nationalities (Nat. Sci. Edition), vol. 23, No. 3, pp. 12-16, Sep. 2004.

ZenMed: "Rosacea treatment systems from ZenMed" Jul. 29, 2008, XP002571925 Retrieved from the Internet: URL:http://web.archive.org/web/20080729052452/zenmed.com/skincare/rosacea/.

Clinique: "Redness Solutions Redness Regime" Apr. 3, 2008, XP002571926 Retrieved from the Internet: URL:http://web.arcive.org/web/20080403232732/http://www.clinique.co.uk/templates/products/sp_nonshaded.tmpl?.

Webster G F: "Treatment of Rosacea" Seminars in Cutaneous Medicine and Surgery, W.B. Saunders, Philadelphia, US, vol. 20, No. 3, Sep. 1, 2001, p. 207-208, XP009056535 ISSN: 1085-5629.

ZenMed: "How does the ZenMed Skin Support System Work? How does this system treat Rosacea?" Retrieved on line [Nov. 10, 2013] from: https://zenmed.com/skincare/rosacea/theSystem.aspx?zl=1, 4 pages.

Culp, Brittney et al., "Rosacea: A Review", P&T, vol. 34, No. 1, pp. 38-45, Jan. 2009.

* cited by examiner

ROSACEA TREATMENTS AND KITS FOR PERFORMING THEM

CROSS-REFERENCE TO RELATED APPLICATIONS

This application is a continuation which claims the benefit of and priority to U.S. patent application Ser. No. 13/144833, filed Jul. 15, 2011 which is a U.S. National Stage Application filed under 35 U.S.C. §371(a) of International Application No. PCT/US2010/021995, which claims the benefit of and priority to U.S. Provisional Application Nos. 61/146,960, filed on Jan. 23, 2009 and 61/225,041 filed on Jul. 13, 2009.

TECHNICAL FIELD

The present disclosure relates to compositions and methods for the treatment of rosacea.

BACKGROUND

Rosacea is a chronic inflammatory disease that occurs primarily in fair skinned people. By some recent estimates rosacea afflicts 13 million Americans. It usually first appears as subtle reddening on the face. Over time this may develop into inflammation, be accompanied by skin eruptions, and in the appearance of red lines which result from swollen or damaged veins and capillary blood vessels immediately under the surface of the skin.

There is no single test to determine whether someone has rosacea. The diagnosis is usually made based on a visual examination and from identifying a number of symptoms, such as: flushing or blushing that occurs easily and often and lasts longer than normal; erythema (i.e., rashes and redness on part or all of the face); burning or stinging sensations; papules, or pustules; rhinophyma; and/or telangiectasis caused as a result of capillary blood vessels in the face becoming enlarged or damaged. Symptoms are often aggravated by sun exposure, changes or extremes in temperature, wind, and consumption of certain foods (including spicy foods, caffeine & alcohol).

Rosacea is generally categorized into four stages. Stage one is characterized by flushing or redness (known as erythema) that lasts for hours or days. Red lines (a condition known as telangiectases) may appear. Stages two and three, Papulopustular and Phymatous, are characterized by skin eruptions (nodules, papules pustules). Symptoms may spread from the face to other parts of the body such as the scalp, neck, and chest. Stage four, Ocular, is characterized by large nodules appearing, severe inflammation, facial pain, swelling, and burning. Rhinophyma the bulbous enlargement of the nose may also be present with some subjects.

The exact cause of rosecea is still largely unknown, however the symptoms are reasonably well understood as are a variety of lifestyle factors (such as particular foods and activities) that are known to trigger outbreaks in people that have the disease. Although there is not yet a cure for rosacea, a combination of treatment of the symptoms and lifestyle changes to avoid these triggers can greatly reduce the negative impacts of rosacea.

In general, the treatment is aimed at the control of redness, inflammation, and skin eruptions. Treatment is necessary to prevent permanent damage and progression of the symptoms. In more severe cases, once a diagnosis of rosacea has been made a dermatologist will prescribed a combination of oral antibiotics and the use of antibiotic gel as initial treatment. The oral antibiotics (e.g., minocycline or erythromycin) will bring the condition under control (reducing redness and the formation of papules and pustules), then the topical treatments will be used to keep the symptoms under control. Since rosacea cannot be cured it is often necessary to continue topical treatment (and modification of lifestyle factors) even after symptoms have been reduced or disappeared. In addition, laser treatments may be employed to seal the broken vessels and prevent blood flow to the surface off the skin. Alternatively, mixed intense pulse light (IPL) may be employed to treat Rosacea symptoms. Light pulse therapy works by sending light energy through the outer skin, concentrating on the dermal layer just below and attacks the problem from the inside, stimulating growth of collagen.

One commercially available treatment for rosacea is Metrogel, from Galderma Laboratories, Fort Worth, Tex. USA. This product is indicated for the topical treatment of inflammatory lesions associated with rosacea and is not clinically approved for reducing redness.

There is thus a continuing need for improved and effectual treatments for rosacea, especially the rapid and effective reduction in redness of the skin associated with rosacea.

SUMMARY

The present disclosure provides a treatment regimen including cleansing at least a portion of an area of skin afflicted with rosacea with a cleanser; applying a composition containing metronidazole to at least a portion of the afflicted area; and applying an anti-redness composition to at least a portion of the cleansed and metronidazole-treated area.

The present disclosure also includes a treatment regimen including cleansing at least a portion of an area of skin afflicted with rosacea with a cleanser; applying a composition containing metronidazole to at least a portion of the afflicted area; applying an anti-redness composition to at least a portion of the afflicted area; and applying a protective composition to at least a portion of the afflicted area.

In another embodiment, the present disclosure provides a kit including an antimicrobial cleanser; a composition containing metronidazole; and an anti-redness composition.

Additionally disclosed is a treatment regimen including cleansing at least a portion of an area of skin afflicted with rosacea with an antimicrobial or cleanser; applying a composition containing a polymetal complex to at least a portion of the cleansed area; and applying a protective composition to at least a portion of the cleansed, and polymetal complex-treated area.

The present disclosure further includes a treatment regimen including cleansing at least a portion of an area of skin afflicted with rosacea with an antimicrobial or cleanser; applying a composition containing a polymetal complex to at least a portion of the cleansed area; and applying a protective composition to at least a portion of the cleansed, and polymetal complex-treated area.

A kit is disclosed in the present disclosure. The kit includes a cleanser; a composition containing a polymetal complex; and a protective composition.

DETAILED DESCRIPTION OF PREFERRED EMBODIMENTS

The present disclosure describes methods for treating skin afflicted with rosacea which include the sequential application of certain products. In embodiments, the disclosure includes sequential application of: a) a cleanser; b) a composition containing metronidazole; c) an anti-redness composition; and, optionally d) a protective composition. In embodiments, the disclosure includes application of a redness-reducing amount of a polymetal complex to at least a portion of the afflicted skin. The polymetal complex may be applied alone, following cleansing and/or in a regimen that also involves the application of a metronidazole-containing composition.

The specific sequence of products applied in accordance with this disclosure will depend on the severity of the rosacea. The present regimens provide better results than any of the individual products used in the regimen and also provide a result that exceeds the sum of the individual results provided by the individual products.

The Cleanser

The cleanser can be any non-soap cleanser that will remove dirt and oil from the skin. Suitable cleansers are commercially available and typically include a combination of anionic, cationic, amphoteric and/or non-ionic surfactants in an aqueous vehicle. The cleanser advantageously can include a combination of compounds to compensate for the well known fact that cleansing agents, by their very nature, are not always well tolerated by the skin. The oil-removal feature of a cleanser can result in drying of the skin, and even skin irritation. By incorporating various protective agents in the cleanser process the preferred cleanser overcomes shortcomings found in many alternative products. Thus, in one particularly useful embodiment the cleanser is a foaming gel cleanser that contains water, sodium lauroyl oat amino acids, cocamidopropyl betaine, sodium laureth sulfate, aloe barbadensis leaf juice, medicago sative (alfalfa) extract, borago officinalis extract, chamomilla recutita (matricaria) extract, sodium chloride, xanthan gum, saponins, phenoxyethanol, methylparaben, propylparaben, ethylparaben, butylparaben, fragrance, and color. In embodiments, the cleanser frees the skin of pollutants without damaging the skin's own natural moisture content. It also leaves all skin types clean and extremely soft to the touch.

In embodiments, in addition to removing dirt and oil from the skin, the cleanser also reduces the skin bacterial count. Such antimicrobial or antibiotic cleanser may include an antimicrobial or antibiotic compound. The antimicrobial or antibiotic compounds employed in the cleanser are not particularly limited. Examples of such antimicrobial or antibiotic compounds include, but are not limited to: chlohexidine gluconate, quaternary ammonia type compounds, alcohol based cleansers (ethanol, isopropyl alcohol, etc.), triclosan, zinc pyrithione, sodium sulphacetamide, clindamycin phosphate, and the like. It is envisioned that one or more antimicrobial agents may be used.

In embodiments, one suitable foaming gel cleanser contains a combination of water, cocamidopropyl betaine, sodium lauroyl oat amino acids, sodium laureth sulfate, glycerin, aloe barbadensis gel, glycerth-7, apricot triethanolamine, sage extract, borage extract, phenoxythanol, methylparaben, propylparaben, ethylparaben, butylparaben, saponins, fragrance, and colorant.

The Composition Containing Metronidazole

In embodiments, a composition containing metronidazole is applied to the cleansed skin of the person afflicted with rosacea.

Metronidazole is a nitroimidazole used in the treatment of infections caused by susceptible organisms, particularly anaerobic bacteria and protozoa. Metronidazole is a prodrug. It is converted in anaerobic organisms by the redox enzyme pyruvate-ferredoxin oxidoreductase. The nitro group of metronidazole is chemically reduced by ferredoxin (or a ferredoxin-linked metabolic process) and the products are responsible for disrupting the DNA helical structure, thus inhibiting nucleic acid synthesis. Metronidazole is selectively taken up by anaerobic bacteria and sensitive protozoal organisms because of the ability of these organisms to reduce metronidazole to its active form intracellularly.

The composition containing metronidazole can be formulated in any manner to provide delivery of the active to the skin of a patient afflicted with rosacea. In embodiments, the composition containing metronidazole contains from about 0.001 to about 5 percent metronidazole by weight of the composition, in embodiments from about 0.1 to about 3 percent metronidazole by weight of the composition, in other embodiments from about 0.5 to about 1.5 percent metronidazole by weight of the composition.

Metronidazole is commercially available as a gel preparation for the treatment of dermatological conditions such as rosacea. Illustrative commercially available compositions containing metronidazole are available under the tradename METROGEL® from Galderma Laboratories, Fort Worth, Tex. USA. In fact, METROGEL is available from Galderma Laboratories in a kit with a gentle skin cleanser commercially available under the tradename CETAPHIL®.

Anti-Redness Composition

Optionally, an anti-redness composition may be applied. The anti-redness composition is a composition containing one or more ingredients that result in redness reduction of the skin, either via a clinical and/or visual manner. The anti-redness composition may include botanicals, calming agents, anti-microbial agents, anti-inflammatory compounds, anti-oxidants, antiseptics, conditioning agents, light refracting materials and the like. Non-limiting examples of such ingredients include Aloe Barbadensis Leaf juice, Hydrolyzed Oat Protein, Bisabolol, Allantoin, Avena Sativa (Oat) Beta Glucan, Avena Sativa (Oat), Kernel Extract, Glycyrrhiza Glabra root extract, Sea Whip Extract, Mica, Titanium Dioxide, Iron Oxides, Bacopa Monniera Extract, Arnica Montana (Flower) Extract, Cupressus Sempervirens (Seed) Extract, Polygontum Multiflorum Extract, Sodium Cocoyl Amino Acid, Sarcosine, Potassium Aspartate, Magnesium Aspartate, Lavandula Angustifolia (Lavender) Flower/leaf Stem Extract, and Malonic Acid.

The Protective Composition

Suitable protective compositions include any composition capable of reducing skin damage, darkening, or dryness. In embodiments, protective compositions include sun block or sunscreen to filter out ultraviolet light rays. A wide variety of sunscreen actives are useful herein. The exact amount and type of sunscreen that is used depends on the level of photoprotection that is desired. Generally any agent offering protection against ultraviolet radiation by absorbing, scattering or reflecting the ultraviolet radiation may be used herein. The sunscreen agents used herein may offer protection against one or more of the following forms of solar radiation: UVA; UVB; UVC; visible light; and infrared radiation. Generally the sunprotection factor (SPF) of the final formulation varies between 2 and 30, although products with SPFs up to 100 may be formulated. The sunscreen used herein may offer chemical or physical photoprotection.

Sunscreens which may be used in accordance with the present invention include those selected from the group comprising amino benzoic acid and derivatives, such as para-amino benzoic acid (PABA), glyceryl-PABA (Lisadimate), Padimate O, Roxadimate; anthrinalates, including methylanthrynilate; benzophenones, including dioxybenzone, oxybenzone and sulisobenzone, 3-benzophenone (Uvinul M40) 4-N,N-dimethylaminobenzoic acid ester with 2,4-dihydroxybenzophenone; camphor derivatives including 3-(4-methylbenzylidene) camphor, 3-benzylidene camphor; cinnamates including DEA-p-methoxycinnamate, ethyl-hexyl p-methoxy cinnamate, octocrylene, octyl methoxy cinnamate (Parasol MCX); dibenzoyl methanes including butylmethoxydibenzoylmethane (Parsol 1789), salicylates including, homomenthyl salicylate, octyl salicylate, trolamine methyl salicylate; metal oxides including titanium dioxide, zinc oxide and iron oxide; 2-phenylbenzimidazole-5-sulfonic acid; 4,4-methoxy-t-butyldibenzoylmethane; and mixtures thereof.

In embodiments, suitable protective compositions include creams, such as moisturizers formulated to help control dryness. In embodiments, the protective composition includes at least one of the following compounds: ZnO; Vitamin A; Vitamin D; and combinations thereof. Optionally, an anti-parasitic product may also be applied for more severe cases, for example, for the control of Dermodex mites.

In embodiments, the anti-parasitic product includes an anti-parasitic compound (such as, for example, pediculicidal or mticidal compounds) that eradicate organisms (such as, for example, ectoparasites, e.g., demodex follicular mites, or endoparasites) that inhabit hair follicles and/or the pores of the skin. Any conventional anti-parasitic compound may be employed. Non-limiting examples of suitable pediculicidal agents include natural or other pyrethrins, pyrethroids, permethrin, lindane, malathion, carbaryl, ivermectin and combinations thereof. Suitable miticides are represented by propynyl sulfites, triazapentadienes, chlorinated aromatics and dinitrophenols. In embodiments, the anti-parasitic product may include a combination of benzyl benzoate, and salicylic acid, a combination effective in eradicating skin parasites. Products including anti-parasitic compounds may be particularly useful in regimens for patients having stage two, stage three, and stage four rosacea.

Additional Components

Depending upon the severity of the rosacea, it may be desirable to apply an anti-acne medication to the afflicted skin following the application of the previous compositions. Some examples of useful anti-acne medications include, but are not meant to be limited to, benzoyl peroxide, antibiotics, retinoids, and combinations thereof. In embodiments, compositions containing benzoyl peroxide may be applied to the afflicted area prior to application of the protective compound. This may further reduce the popular and pustular lesions. Suitable benzoyl peroxide compositions may contain, for example, from about one percent to about ten percent by weight benzoyl peroxide.

In other embodiments it may be desirable to apply a composition containing a retinoid to the afflicted area after application of the protective compound. The term retinoid is intended to embrace any compound that binds to or otherwise interacts with a retinoid receptor. Suitable retinoids include retinol, retinoic acid, retinyl palmitate, retinyl propionate, retinyl acetate, tretinoin, isotretinoin, motretinide, adapalene, tazarotene, azelaic acid, as well as synthetic retinoid mimetics.

Although not wishing to be bound by this disclosure, it is believed that tretinoin passes through the skin cell membranes to the nucleus wherein it binds to nuclear receptors and regulates transcription of genes that mediate the rate of cell division and turnover, cell differentiation, formulation of new healthy collagen, and the repair of elastin. As a result, skin can be made firmer by the collagen formation as well as more flexible from the repair of elastin.

Tretinoin also increases the formation of normal keratinocytes (cells making up about 90% of the epidermis) and fibroblasts (connective tissue cells which secrete an extracellular matrix rich in collagen and other macromolecules), decreases melanocyte activity (which offers better resistance to external injury and inflammation) and is found to improve angiogenesis (the formation of new blood vessels that increase skin circulation).

In still other embodiments, it also may be desirable to apply a composition containing an antibiotic to the afflicted area after application of the protective compound. Any antibiotic known to have a beneficial effect upon the skin may be employed. In embodiments, the antibiotic used is clindamycin, tetracycline, erythromycin or combinations thereof. The antibiotic may be applied topically to the afflicted skin or administered in another manner, such as orally to the subject suffering from rosacea.

The various products applied in a regimen in accordance with the present disclosure can be in the form of solutions, emulsions (including microemulsions), suspensions, creams, lotions, gels, powders, or other typical solid or liquid compositions used for treatment of age related skin conditions. Such compositions may contain, in addition to the specific active(s) identified herein for each product, other ingredients typically used in such products, such as antimicrobials, moisturizers and hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents and water, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

Polymetal Complex

The present disclosure also describes methods for treating skin afflicted with rosacea which include the step of applying a redness-reducing amount of a polymetal complex to at least a portion of the afflicted skin. In embodiments, the polymetal complex, e.g., Cu/Zn malonate is combined with a moisturizer and applied to the afflicted skin. The polymetal complex may be applied alone, following cleansing, or as a moisturizer. When used in the present regimens as a moisturizer, the polymetal complex improves capillary elasticity.

The polymetal complex can be the reaction product of a polyfunctional compound with two or more coordination elements. The preparation of reaction products of polyfunctional compounds with two or more coordination elements and compositions containing such reaction products are described. In embodiments, the resulting polymetal complex includes a first metal ion, a second metal ion that is different from the first metal ion and a central bridging unit linking the first and second metal ions, the central bridging unit being derived from a polyfunctional compound of the type described herein.

The polyfunctional compound can be any compound that contains at least two functional groups that may complex with metal cations in solution. Among the functional groups that may be present include carboxylic acid groups and amino groups. Suitable polyfunctional compounds include, but are not limited to polyfunctional acids, polyfunctional amines and amino acids. Other suitable polyfunctional compounds will be readily envisioned by those skilled in the art reading the present disclosure. It should of course be understood that mixtures of polyfunctional compounds may be used.

Polyfunctional acids are primarily monomeric compositions having two or more carboxylic acid groups. Non-limiting examples of polyfunctional acids include maleic acid, fumaric acid, citraconic acid, itaconic acid, glutaconic acid, phthalic acid, isophthalic acid, terephthalic acid, cyclohexane dicarboxylic acid, citric acid, succinic acid, adipic acid, sebacic acid, azealic acid, malonic acid, dodecanedioic acid, 1,18-octadecanedioic acid, dimer acids (prepared from a mono-, di- or triunsaturated fatty acid, acid wax, acid anhydride grafted wax, or other suitable polycarboxylic acid reacting compound), alkenyl succinic acids (such as n-dodecenylsuccinic acid, docecylcucinic acid and octadecenylsuccinic acid). Polysaccharides having two or more carboxylic groups can be used as the polyfunctional acid compound. Thus, for example, hyaluronic acid may be used as the polyfunctional compound. The polyfunctional acid can be present in acidic form, anhydride form, salt form, or mixtures thereof. Any derivative of any polyfunctional acid can be used provided the derivative still contains two carboxylic acid groups. In embodiments, the polyfunctional acid chosen as the polyfunctional compound contains exactly two carboxylic acid groups.

Amino acids may also be used as the polyfunctional compound. Amino acids are known to those skilled in the art and include at least a carboxylic acid functionality and an amino functionality. In embodiments, the amino acid chosen as the polyfunctional compound contains two carboxylic acid groups. Suitable amino acids include naturally occurring amino acids and synthetic amino acids. Non-limiting examples of amino acids include, but are not limited to: aminopolycarboxylic acids (e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, β-aminopimelic acid, 2-aminosuberic acid and 2-aminosebacic acid); amino acid amides such as glutamine and asparagine; polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid; other basic amino acid residues such as histidine; diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid; imino acids such as proline, hydroxyproline, allohydroxyproline, γ-methylproline, pipecolic acid, 5-hydroxypipecolic acid, and azetidine-2-carboxylic acid; mono- or di-alkyl (typically $C_1$-$C_8$ branched or normal) amino acids such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-ethyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, aaminodiisoamyacetic acid, α-methylaspartic acid, α-methylgiutamic acid, 1-aminocyclopropane-1-carboxylic acid, isoleucine, alloisoleucine, tert-leucine, β-methyltryptophan and α-amino-β-ethyl-β-phenylpropionic acid; β-phenylserinyl; aliphatic α-amino-β-hydroxy acids such as serine, β-hydroxyieucine, β-hydroxynorleucine, β-hydroxynorvaline, and α-amino-β-hydroxystearic acid; α-Amino, α-, γ-, δ- or ε-hydroxy acids such as homoserine, γ-hydroxynorvaline, δ-hydroxynorvaline and epsilon-hydroxynorleucine residues; canavine and canaline; γ-hydroxyornithine; 2.hexosaminic acids such as D-glucosaminic acid or D-galactosaminic acid; α-Amino-β-thiols such as penicillamine, β-thiolnorvaline or β-thiolbutyrine; other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine; phenylalanine, tryptophan and ring-substituted a amino acids such as the phenyl- or cyclohexylamino acids α-aminophenylacetic acid, aaminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dicloro, o-, m- or p-methyl-, 2,4,6-trimethyl-, 2-ethoxy-5-nitro-, 2-hydroxy-5-nitro- and p-nitrophenylalanine); furyl-, thienyl-, pyridyl-, pyrimidinyl-, purinyl- or naphthylalanines; and tryptophan analogues and derivatives including kynurenine, 3-hydroxykynurenine, 2-hydroxytryptophan and 4-carboxytryptophan; α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine. glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Aminopolycarboxylic acids, e.g., aspartic acid, β-hydroxyaspartic acid, glutamic acid, β-hydroxyglutamic acid, β-methylaspartic acid, β-methylglutamic acid,β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid. Polyaminoacids may also be used provided they form complexes with the coordination elements employed.

The polyfunctional compound is reacted with two or more coordination elements. The coordination elements can be chosen from the elements listed in Groups IIIA to VIIIA, Groups IB to IIIB, of periods 4 and 5 and aluminum in Group IIIB, period 3 of The Periodic Table of the Elements. Suitable non-limiting examples of elements listed in group IB of The Periodic Table of Elements include copper, silver, and gold. Suitable non-limiting examples of coordination elements include aluminum, scandium, titanium, vanadium, chromium, manganese, iron, cobalt, nickel, copper, zinc, gallium, yttrium, zirconium, niobium, molybdenum, technetium, ruthenium, rhodium, palladium, silver, cadmium, and indium. Tin may also be used. Those skilled in the art will readily envision suitable compounds for providing the coordination elements in solution. In embodiments, the coordination element is provided for the reaction as a basic salt that can participate in an acid-base reaction with a polyfunctional compound containing two carboxylic acid groups.

In embodiments, the polymetal complex is a copper-zinc malonate. Copper-zinc malonates may be one or more ionic compounds formed by joining one or more independent copper molecules or ions and one or more independent zinc molecules or ions to a central unit by ionic bonds. For example, the copper-zinc malonate may be in the form of a trinuclear cation, where structurally independent copper and zinc hydrates are bridged by a central unit such as an octahedral diaquadimalonatocopper (II) unit. However, various coordination modes are possible depending on the source of the copper and zinc and synthesis conditions. In embodiments, the central unit malonate ion may be a multi-membered ring such as eight-membered ring, six-membered ring, and four-membered metalocycle for bridging or chelating functions between the copper and zinc constituents. Accordingly, the crystal structures of copper-zinc malonates can be very diverse, from ionic to three-dimensional polymers. In embodiments, the copper-zinc malonates can be found in several hydrate, and polymorphic forms. Suitable copper-zinc malonate forms in accordance with the present disclosure include any salt formed from the neutralization of malonic acid by one or more copper containing molecules and one or more zinc containing molecules. In embodiments, copper and zinc are provided for the reaction as basic salts that can participate in an acid-base reaction with the two carboxylic acid groups present in malonic acid. Illustrative examples include salt formed by the neutralization of malonic acid by cupric carbonate ($CuCO_3Cu(OH)_2$), and zinc carbonate ($3Zn(OH)_2 \cdot 2ZnCO_3$) in an aqueous solution.

It has been discovered that the compositions which contain the polymetal complex are useful in causing varying levels of vasoconstriction. Such an effect may be useful in treating rosacea. Moreover, the vasoconstrictive effect of the present compositions decrease the rate at which the body is able to clear the composition by local blood supply, thereby allowing the composition to remain at the site of application longer which increases the rate and depth of tissue penetration of the composition. In embodiments, the compositions of the present application may be combined with other vasoconstrictive agents to further enhance the effect of the polymetal complex. In still other embodiments, the compositions of the present application may be combined with vasodilating agents thereby decreasing the effect of the polymetal complex.

In embodiments, the polymetal complex may be combined with numerous ingredients to form products that can be applied to the skin of a person afflicted with rosacea. Such products may include a dermatologically or pharmaceutically acceptable carrier, vehicle or medium, for example, a carrier, vehicle or medium that is compatible with the tissues to which they will be applied. The term "dermatologically or pharmaceutically acceptable," as used herein, means that the compositions or components thereof so described are suitable for use in contact with these tissues or for use in patients in general without undue toxicity, incompatibility, instability, allergic response, and the like. In embodiments, compositions in accordance with the present disclosure can contain any ingredient conventionally used in cosmetics and/or dermatology. In embodiments, active ingredients may be formulated to provide crystals in solution, as well as solid forms. Methods of making the polymetal complex and formulating topical compositions containing them are described, for example, in published patent applications US-2007-0191620-A1, US-2007-0203354-A1, US-2007-0184017-A1, US-2007-0190190-A1, US-2008-0081077-A1, the entire contents of which are all incorporated herein by this reference.

In embodiments, products containing a polymetal complex in accordance with the present disclosure as an active ingredient can be in the form of solutions, emulsions (including microemulsions), suspensions, creams, lotions, gels, powders, or other typical solid or liquid compositions used for treatment of age related skin conditions. Such compositions may contain, in addition to the reaction product in accordance with this disclosure, other ingredients typically used in such products, such as antimicrobials, moisturizers and hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents and water, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

As an illustrative example, products can be formulated to contain copper-zinc malonate in amounts from about 0.001 to about 5% by weight of the total composition. In embodiments, products can be formulated to contain copper-zinc malonate in an amount from about 0.05 to about 1.0% by weight of the total composition. In other embodiments, the amount of copper-zinc malonate is from about 0.1 to about 0.5% by weight of the total composition. Here, the copper-zinc malonate present may be in a pharmaceutically acceptable salt form. Other active ingredients may be provided in the formulations at the same concentrations.

Table A below provides an illustrative embodiment of a suitable composition containing a polymetal complex in accordance with the present disclosure.

TABLE A

| Ingredient | Decsription (function) | Amount |
|---|---|---|
| Water Phase | | |
| Distilled Water | (solvent, humectant) | 69.4940 |
| PHENONIP | Phenoxyethanol, Methylparaben, Ethylparaben, Butylparaben, Propylparaben, Isobutylparaben (preservative) | 0.8000 |
| Propylene Glycol | (humectant) | 1.5000 |
| Glycerin | (humectant) | 2.5000 |
| Veegum Granules | Magnesium Aluminum Silicate (suspending agent) | 0.4000 |
| Keltrol CG | Xanthan Gum (viscosity building agent) | 0.6000 |
| Oil Phase | | |
| Finsolv TPP | $C_{12-15}$ Alkyl Benzoate; Dipropylene Glycol Dibenzoate, PPG - 15 Stearyl Ether Benzoate, 50%/35%/15%; 2.25%/1.575%/0.75% (emollient) | 4.5000 |
| GE Silicone SF 1214 | Cyclopentasiloxane, Dimethicone, 80/20; 2.4%/0.6% (emollient) | 3.0000 |
| Gemseal 25 | $C_{13-15}$ Alkane (emollient) | 3.0000 |
| Pelemol OP | Ethylhexyl Palmitate (emollient) | 3.0000 |
| Lipomulse 165 | Glyceryl Stearate, PEG-100 Stearate 2.475%/2.025% (emulsifier) | 4.5000 |
| Cetyl Alcohol | (thickener) | 0.5000 |
| Stearyl Alcohol | (thickener) | 1.5000 |
| GE Silicone 96-100 | Dimethicone (emollient) | 1.0000 |

TABLE A-continued

| Ingredient | Decsription (function) | Amount |
|---|---|---|
| Abil Wax | Cetyl Dimethicone (emollient) | 0.1000 |
| Vitamin E Acetate | (vitamin) | 0.0500 |
| Engelhard Flamenco Satin Green P860 | Mica, Titanium Dioxide, Iron Oxides (pigments) | 0.0100 |
| Kobo BPD 500 | HDI/Trimethylol Hexyllactone Crosspolymer, Silica | 0.0100 |
| Presperse - Coverleaf AR-80 | Talc, Titanium Dioxide, Alumina, Silica (pigments) | 0.0010 |
| Copper-Zinc Malonate | (active) | 2.5000 |
| Sepigel 305 | Polyacrylamide, $C_{13-14}$ Isoparaffin, Laureth - 7 (viscosifier/suspending agent) | 1.0000 |
| Extract Blend | Algae Extract, *Glycyrrhiza Clabra* Root Extract (antioxidants) | 0.0100 |
| Blueberry Fruit Extract | (antioxidants) | 0.025 |
| 8% NaOH Solution | (ph adjusting agent) | QS |
| 10% Malonic Acid Solution | | QS |

In embodiments, regimens for treatment of rosacea involve the sequential application of a series of products to the skin of a person afflicted with rosacea. The specific sequence of products applied in accordance with this disclosure will depend on the severity of the rosacea. The regimens for treating rosacea described herein may include the application of a composition containing a polymetal complex and may further include the application of one or more of the following: an antibiotic or antimicrobial cleanser, a protective composition, an anti-parasitic product and various combinations thereof. In embodiments, the cleanser is applied to at least a portion of the afflicted skin prior to the application of the composition containing a polymetal complex. In embodiments, the protective composition is applied to at least a portion of the afflicted skin following the application of a composition containing a polymetal complex.

In still other embodiments, at least three products may be used to treat the afflicted skin. The three products applied may be an antimicrobial or antibiotic cleanser, a composition containing a polymetal complex, and a protective composition. In embodiments, the composition containing a polymetal complex contains Cu/Zn malonate.

As the rosacea treatment regimens described herein require the sequential application of various components, it has also been found that kits greatly facilitate the user in performing the treatment regimen consistently. With respect to the composition containing metronidazole, the composition is currently a prescription medication that can be procured in addition to the kit or as a prescription kit. However, in the future if a composition containing metronidazole becomes an over-the-counter product, inclusion in a non-prescription kit is contemplated. One suitable kit for rosacea treatment includes the following:

> Antimicrobial-containing cleanser
> Anti-Redness Composition
> Sunscreen with ZnO and vitamins A and D
> Optionally one or more of:
> Benzoyl Peroxide Composition
> Retinoid Composition
> Antibiotic Composition In embodiments, the kit contains:

> A cleanser
> A composition containing a polymetal complex
> A protective composition
> Sunscreen with ZnO and vitamins A and D
> Optionally one or more of:
> Benzoyl Peroxide Composition
> Retinoid Composition
> Antibiotic Composition
> composition containing metronidazole In other embodiments, the kit contains:

> A cleanser
> A composition containing a polymetal complex
> A composition containing metronidazole
> An anti-redness composition
> A protective composition In yet other embodiments, the kit contains:

> Antimicrobial containing cleanser
> Product containing anti-parasitic compounds
> Moisturizer with Cu/Zn malonate
> Sunscreen with ZnO and vitamins A and D
> Optionally one or more of:
> Benzoyl Peroxide Composition
> Retinoid Composition
> Antibiotic Composition An illustrative regimen in accordance with the present disclosure is as follows:

| AM | PM |
|---|---|
| Gentle Cleanser | Gentle Cleanser |
| Metronidazole Gel 0.75% | Metronidazole Gel 0.75% |
| Anti-Redness Composition (Hydrating Complexion Corrector) | Anti-Redness Composition (Hydrating Complexion Corrector) |
| Skin Balancing Sun Protection SPF 30 | |

In embodiments, a regimen in accordance with the present disclosure is as follows:

| AM | PM |
|---|---|
| Gentle Cleanser | Gentle Cleanser |
| Metronidazole Gel 0.75% | Metronidazole Gel 0.75% |
| Moisturizer with Cu/Zn malonate | Moisturizer with Cu/Zn malonate |
| Anti-Redness Composition (Hydrating Complexion Corrector) | Anti-Redness Composition (Hydrating Complexion Corrector) |
| Skin Balancing Sun Protection SPF 30 | |

Typically, kits are provided with instructions for care. For example, the instructions may direct that the various compositions of the pre-procedure treatment regimen be applied as follows:

| Rosacea type | Product 1 | Product 2 | Product 3 | Product 4 | Product 5 |
|---|---|---|---|---|---|
| Type 1 (mild) | cleanser | Moisturizer with Cu/Zn malonate | Sunscreen based on ZnO and Vitamin A&D | | |
| Type 2 (moderate) | cleanser | Moisturizer with Cu/Zn malonate | Sunscreen based on ZnO and Vitamin A&D | Anti parasitic product 1% BPO lotion | Retinoic acid |
| Type 3 (severe) | cleanser | Moisturizer with Cu/Zn malonate | Sunscreen based on ZnO and Vitamin A&D Sunscreen | Anti parasitic product 1% BPO lotion | Oral minocycline or tetracycline antibiotic |

The rosacea treatment regimen involves applying designated products in the smallest possible amount sufficient to cover at least a portion of the site afflicted with rosacea. In embodiments, the designated products may also be applied to the entire face of the patient even if only a small area of the face is afflicted with rosacea.

EXAMPLES

Example 1

An anti-redness composition suitable for use in the presently described regimen is prepared having the composition shown in Table B. The composition is prepared by combining the Water Phase ingredients in a reaction vessel with heating to 70 to 75° C. and stirring. The Oil Phase ingredients are combined in a separate reaction vessel with heating to 70-75° C. and stirring. The Oil Phase is then added to the Water Phase with continued stirring until a homogeneous dispersion is achieved. The Additional Ingredients are then added with stirring.

TABLE B

| Ingredients | Percent | INCI Names | Functionality |
|---|---|---|---|
| Water Phase | | | |
| Distilled Water | 54.08 | Water | Solvent, Moisturizer |
| Phenonip | 1.00 | Phenoxyethanol, Methylparaben, Ethylparaben, Butylpraben, Propylparaben, Isobutylparaben | Preservative |
| Carbowax 300 | 2.25 | PEG - 6 | Humectant, solvent |
| Glycerin | 0.50 | Glycerin | Humectant, skin conditioner |
| Di-Propylene Glycol | 2.25 | Dipropylene Glycol | Humectant, solvent |
| Keltrol CG | 0.25 | Xanthan Gum | Suspending agent, thickener |
| Veegum | 0.15 | Magnesium Aluminum Silicate | Suspending agent, thickener |
| Oil Phase | | | |
| Pelemol OP | 2.75 | Ethylhexyl Palmitate | Emollient |
| Pelemol ICB | 1.50 | Isocetyl Behenate | Emollient |
| Cetiol LC | 2.75 | Coco-Caprylate/Caprate | Emollient |
| Permethyl 101A | 4.50 | Isohexadecane | Emollient |
| Gemseal 25 | 1.00 | C13-15 Alkane | Emollient |
| Lipomulse 165 | 2.50 | Glyceryl Stearate, PEG 100 Stearate | Emulsifier |
| Cetyl Alcohol | 0.50 | Cetyl Alcohol | Thickener, emulsion stabilizer |
| Stearyl Alcohol | 1.50 | Stearyl Alcohol | Thickener, emulsion stabilizer |
| GE Slicone 96-100 | 1.00 | Dimethicone | Skin Protectant |
| Vitamin E Acetate | 0.05 | Tocopheryl Acetate | Anti-Oxidant |
| Titanium Dioxide MT-500B | 5.00 | Titanium Dioxide | Opacyfing and covering agent |
| Coverleaf AR 80 | 2.00 | Talc, Titanium Dioxide, Alumina, Silica | Soft focus characteristic |
| Simulgel INS 100 | 2.00 | Hydroxyethyl Acrylate/Sodium Acryloldimethyl Tauarte Copolymer, Isohexadecane, Polysorbate 60 | Emulsifier, thickener |
| Additional Ingredients | | | |
| Soft Tex Yellow Iron Oxide C337773 | 0.03 | Iron Oxide | Tinting/coloring ingredient |
| Soft Tex Red Iron Oxide C337775 | 0.03 | Iron Oxide | Tinting/coloring ingredient |
| Soft Tex Black Iron Oxide C337734 | 0.02 | Iron Oxide | Tinting/coloring ingredient |
| Water | 3.00 | Water | Solvent, moisturizer |

Example 2

A protective composition suitable for use in the presently described regimen is prepared having the composition shown in Table C. The composition is prepared by combining the Water Phase ingredients in a reaction vessel with heating to 70-75° C. and stirring. The oil phase ingredients are combined in a separate reaction vessel with heating to 70-75° C. and stirring. The oil phase is then added to the water phase with continued stirring until a homogenous dispersion is achieved. The additional ingredients are then added with stirring.

TABLE C

| Ingredient | | Percent | INCI Name | Functionality |
|---|---|---|---|---|
| Aqueous Phase | | | | |
| Water | | 50.0550 | Water | Solvent, moisturizer |
| Glycerin | | 0.5000 | Glycerin | Humectant, skin conditioner |
| Dipropylene Glycol | | 10.0000 | Dipropylene Glycol | Humectant, solvent |
| CARBOWAX 300 ® | | 3.0000 | PEG-6 | Humectant, solvent |
| PHENONIP ® | | 1.0000 | Phenoxyethanol, Methylparaben, Propylparaben, Ethylparaben, Butylparaben, Isobutylparaben | Preservative |
| Oil Phase | | | | |
| MONTONOV ® 82 | | 2.0000 | Cetearyl Alcohol, Cocoa Glucoside | |
| PERMETHYL 101A ® | | 0.3000 | Isohexadecane | Emollient |
| KOBO TNP5OzSI | 11.28% Zinc Oxide (47%) | 24.0000 | C12-15 Alkyl Benzoate, Zinc Oxide, Polyhydroxystearic Acid, Triethoxycaprylsilane | Sunscreen |
| Vitamin E Acetate | | 0.0500 | Tocopheryl Acetate | Anti-Oxidant |
| Z COTE ® | 4.5% Zinc oxide | 4.5000 | Zinc Oxide | Sunscreen, Skin Protectant |
| Micro Titanium Dioxide MT 500B | | 1.8000 | Titanium Dioxide | Sunscreen |
| Kobo TNP40VTTS | 0.32% Titanium Dioxide (32%) | 1.0000 | C12-15 Alkyl Benzoate, Titanium Dioxide, Alumina, Polyhydroxystearic Acid, Isopropyl Titanium Triisostearatel Triethoxycaprylysilane Crosspolymer | Sunscreen |
| Additional Ingredients | | | | |
| Flamenco satin Green 860 M | | 0.2500 | Mica, Titanium Dioxide, Iron Oxides | Helps to diminish skin redness |
| Soft Tex Yellow Iron Oxide C337773 | | 0.0200 | Iron Oxide | Tinting masstone |
| Soft Tex Red Iron Oxide C337775 | | 0.0150 | Iron Oxide | Tinting masstone |
| Soft Tex Black Iron Oxide C337734 | | 0.0100 | Iron Oxide | Tinting masstone |
| Sepinov EMT 10 | | 1.5000 | Hydroxyethylacrylate/Sodium Acrylolyldimethyl Taurate | Emulsifier |

Example 3

Another protective composition suitable for use in the presently described regimen is prepared having the composition shown in Table D. The composition is prepared by combining the Water Phase ingredients in a reaction vessel with heating to 70-75° C. and stirring. The oil phase is then added to the water phase with continued stirring until a homogeneous dispersion is achieved.

TABLE D

| Ingredient | | Percent | INC Name | Functionality |
|---|---|---|---|---|
| Aqueous Phase | | | | |
| Water | | 50.0550 | Water | Solvent, moisturizer |
| Glycerin | | 0.5000 | Glycerin | Humectant, skin conditioner |
| Dipropylene Glycol | | 10.0000 | Dipropylene Glycol | Humectant, solvent |
| CARBOWAX 300 ® | | 3.0000 | PEG-6 | Humectant, solvent |
| PHENONIP ® | | 1.0000 | Phenoxyethanol, Methylparaben, Propypylparaben, Ethylparaben, Butylparaben, Isobutylparaben | Preservative |
| Oil Phase | | | | |
| MONTONOV ® 82 | | 2.0000 | Cetearyl Alcohol, Cocoa Glucoside | |
| PERMETHYL 101A ® | | 0.3000 | Isohexadecane | Emollient |
| KOBO TNP5OzSI | 11.28% Zinc Oxide (47%) | 24.0000 | C12-15 Alkyl Benzoate, Zinc Oxide, Polyhydroxystearic Acid, Triethoxycaprylsilane | Sunscreen |
| Vitamin E Acetate | | 0.0500 | Tocopheryl Acetate | Anti-oxidant |
| Z COTE ® | 4.5% Zinc oxide | 4.5000 | Zinc Oxide | Sunscreen, Skin Protectant |
| Micro Titanium Dioxide MT 500B | | 1.8000 | Titanium Dioxide | Sunscreen |

TABLE D-continued

| Ingredient | Percent | | INC Name | Functionality |
|---|---|---|---|---|
| Kobo TNP40VTTS | 0.32% Titanium Dioxide (32%) | 1.0000 | C12-15 Alkyl Benzoate, Titanium Dioxide, Alumina, Polyhydroxystearic Acid, Isopropyl Titanium Triisostearatel Triethoxycaprylysilane Crosspolymer | Sunscreen |
| Additional Ingredients | | | | |
| Flamenco satin Green 860 M | | 0.2500 | Mica, Titanium Dioxide, Iron Oxides | Helps to diminish skin redness |
| Soft tex Yellow Iron Oxide C337773 | | 0.0200 | Iron Oxides | Tinting masstone |
| Soft tex Red Iron Oxide C337775 | | 0.0150 | Iron Oxides | Tinting masstone |
| Soft tex Black Iron Oxide C337734 | | 0.0100 | Iron Oxides | Tinting masstone |
| Sepinov EMT 10 | | 1.5000 | Hydroxyethylacrylate/Sodium Acrylolyldimethyl Taurate | Emulsifier |

Example 4

An additional anti-redness composition suitable for use in the presently described regimen is prepared having the composition shown in Table E. The composition is prepared by combining the Water Phase ingredients in a reaction vessel with heating to 70-75° C. and stirring. The Oil Phase is then added to the Water Phase with continued stirring until a homogeneous dispersion is achieved. The Additional Ingredients are then added with stirring.

TABLE E

| Ingredients | Percent | INCI Names | Functionality |
|---|---|---|---|
| Water Phase | | | |
| Distilled Water | 54.08 | Water | Solvent, Moisturizer |
| Phenonip | 1.00 | Phenoxyethanol, Methylparaben, Ethylparaben, Butylparaben, Propylparaben, Isobutylparaben | Preservative |
| Carbowax 300 | 2.25 | PEG-6 | Humectant, solvent |
| Glycerin | 0.50 | Glycerin | Humectant, skin conditioner |
| Di-Propylene Glycol | 2.25 | Dipropylene Glycol | Humectant, solvent |
| Keltrol CG | 0.25 | Xanthan Gum | Suspending agent, thickener |
| Veegum | 0.15 | Magnesium Aluminurn Silicate | Suspending agent, thickener |
| Oil Phase | | | |
| Pelemol OP | 2.75 | Ethylhexyl Palmitate | Emollient |
| Pelemol ICB | 1.50 | Isocetyl Behenate | Emollient |
| Cetiol LC | 2.75 | Coco-Caprylate/Caprate | Emollient |
| Permethyl 101A | 4.50 | Isohexadecane | Emollient |
| Gemseal 25 | 1.00 | C13-15 Alkane | Emollient |
| Lipomulse 165 | 2.50 | Glyceryl Stearate, PEG 100 Stearate | Emulsifier |
| Cetyl Alcohol | 0.50 | Cetyl Alcohol | Thickener, emulsion stabilizer |
| Stearyl Alcohol | 1.50 | Stearyl Alcohol | Thickener, emulsion stabilizer |
| GE Silicone 96-100 | 1.00 | Dimethicone | Skin Protectant |
| Vitamin E Acetate | 0.05 | Tocopheryl Acetate | Anti-Oxidant |
| Titanium Dioxide MT-500B | 5.00 | Titanium Dioxide | Opacyfing and covering agent |
| Coverleaf AR 80 | 2.00 | Talc, Titanium Dioxide, Alumina, Silica | Soft focus characteristic |
| Simulgel INS 100 | 2.00 | Hydroxyethyl Acrylate/Sodium Acryloldimethyl Tauarte Copolymer, Isohexadecane, Polysorbate 60 | Emulsifier, thickener |
| Additional Ingredients | | | |
| Soft Tex Yellow Iron Oxide C337773 | 0.03 | Iron Oxide | Tinting/coloring ingredient |
| Soft Tex Red Iron Oxide C337775 | 0.03 | Iron Oxide | Tinting/coloring ingredient |
| Soft Tex Black Iron Oxide C337734 | 0.02 | Iron Oxide | Tinting/coloring ingredient |
| Water | 3.00 | Water | Solvent, moisturizer |
| Activera 1-200A | 0.50 | *Aloe Barbadensis* Leaf juice | Soothing, calming agent |
| Hydrolyzed Oat Protein 6-055 LC | 0.50 | Hydrolyzed Oat Protein, water, Glycerin, Phenoxyethanol | Soothing, conditioning agent |
| Bisabolol (lipo) | 0.20 | Bisabolol | Anti-inflammatory, Anti-irritant, anti-microbial |
| Allantoin | 0.50 | Allantoin | Skin Protectant |
| Oat Beta Glucan 6-070 L | 0.25 | *Avena Sativa* (Oat) Beta Glucan, *Avena Sativa* (Oat) Kernel Extract, Phenoxyethanol, Water | Soothing, conditioning |
| Licorice ECO | 0.10 | Glycerin, wate, Glycyrrhiza Glabra root extract | Anti-inflammatory, Energized immune system, Anti-microbial, anti-oxidant. |
| Gorgonian Extract PTG | 0.10 | Pentylene Glycol, Sea Whip Extract | Anti-inflammatory |
| Flamenco Satin Green 860M | 0.25 | Mica, Titanium Dioxide, Iron Oxides | Helps to diminish appearance of red skin |
| Bacocalmine | 2.00 | *Bacopa Monniera* Extract, Water. PEG 8, Hydroxycellulose | Anti-irritation & anti-inflammatory |

TABLE E-continued

| Ingredients | Percent | INCI Names | Functionality |
|---|---|---|---|
| Phytotonine | 2.00 | Propylene Glycol, *Arnica Montana* (Flower) Extract, *Cupressus Sempervirens* (Seed) Extract, *Polygontum Multiflorum* Extract | Increases microcirculation and strengthens vein walls |
| Sepicalm S | 2.00 | Sodium Cocoyl Amino Acid, Sarcosine, Potassium Aspartate, Magnesium Aspartate | Against UV stress, mechanical aggressions, Against inflammation and soothes skin |
| Lavender Extract H0539 | 1.00 | *Lavandula Angustifolia* (Lavender) Flower/leaf Stem extract | Antispetic and anti-inflammatory |
| 5% NaOH solution | | Water, Sodium Hydroxide | Buffering Agent |
| 5% Malonic Acid | | Water, Malonic Acid | Buffering Agent |

Example 5

A 25-day, half-face, randomized study was conducted to determine if the use of a regimen in accordance with the present disclosure decreases the red/irritated skin of Rosacea subjects when compared to untreated skin. Approximately 10 subjects participated in the study. To facilitate enrollment, the qualification visit took place no sooner than 3 days prior to the start of the study. Potential subjects presented with red/irritated skin associated with Rosacea as determined by a Board-Certified Dermatologist during the qualification visit. Subjects with a global assessment score of 4 or greater (using a 10-point scale) with an equal value on the right and left side of the face and who meet the inclusion/exclusion criteria were enrolled. Each subject was required to respond to a baseline questionnaire prior to treatment at Day 0 (baseline). Global tolerability assessments were conduct by a trained evaluator pre- and post treatment during visits Day 0-4, 11 and 18. Tolerability assessments were conducted by a Board-Certified Dermatologist pre- and post-application on Day 25 (final visit). Subjects returned to the testing facility on Days 1-4, and the same procedures were followed as for Day 0. A series of photographs were taken of the right and left side of the face using the VISIA-CR® Image System (Canfield Scientific, Fairfield, N.J.). At all visits to the testing facility, the subjects applied products under the direction and supervision of the technician. The subjects made all PM applications at home, and responded to a questionnaire after the PM application. According to a randomization scheme, subjects were assigned the test products so that odd-numbered subjects applied the test products to the right side of the face, and the left side remained untreated. Even-numbered subjects applied the test products to the left side of the face while the right side of the face remained untreated. Subjects were given daily use instructions and a daily diary to record time of usage and any other safety related comments.

Subjects washed their faces only with the provided cleanser as instructed. Additionally, subjects came to the testing clinic without applying any cosmetic products to the face including moisturizers or facial powder. Ten (10) subjects were enrolled in the study based on the following criteria:

Inclusion Criteria
1. Male/Female 20-68 years of age. Fitzpatrick Skin Type I-III.
2. Moderate to severe (grades 4-9 on 10-point scale) redness/irritation associated with Rosacea uniformly distributed across the right and left side of the face (between and across cheeks). Subjects with papules/pustules preferred.
3. Subjects willing and able to sign the Informed Consent Form, to follow the study directions and to remain in the test facility for approximately 60 minutes at all scheduled visits to the clinic,
4. Female subjects willing to have a urine pregnancy test if not surgically sterile or post-menopausal at least 5 years at screening (baseline) and study end or withdrawal from the study.
5. Subjects free of cuts, burns, scratches or any other condition on the face that, in the opinion of the investigator, may interfere with the proper conduct of the study.
6. Subjects willing to leave ½ side of the face untreated for the entire study.
7. Subjects willing to refrain from excessive sun exposure and refrain from using tanning booths during the entire course of the study.

Exclusion Criteria
1. If female of childbearing potential: Pregnant or lactating as determined by urine pregnancy test if not surgically sterile or post-menopausal at least 5 years.
2. Allergy to benzoyl peroxide or salicylic acid.
3. Any facial skin disease, which can interfere with study results.
4. Sunburn/tan on the face.
5. Make-up on forehead/cheeks.
6. Use of the following medications within the described period (Note: topical refers to facial area):
   A) Medicated facial cleansers, including antibacterial soaps
   —1 week
   B) Topical AHAs and anti-acne medications (BPO, retinoids, antibiotics)—2 weeks
   C) Systemic antibiotics and investigational drugs
   —4 weeks
   D) Participation in a clinical study with OTC or RX drug on the face
   —4 weeks
7. Concurrent use of other medicated products on the face.
8. Concurrent participation in another clinical study.
9. History of cancer on the face.
10. Subjects with other abnormal clinical findings or systemic condition or uncontrolled disease, which the Investigator feels, may put the subject at undue risk or may interfere with the study results.
11. Subjects with blood disorders.
12. Subjects taking Anticoagulants.
13. Subjects taking Disulfiram The study formulations are:
Gentle cleanser commercially availableforrn Obagi Medical Products, Long Beach Calif., USA under the tradename NU DERM® Gentle Cleanser The anti-redness composition of Example 2
The protective composition of Example 1
Metronidazole Topical Gel USP 0.75%

There were a total of compositions used in the study. Each subject received a cleanser, protective composition and anti-redness treatment to be applied to the right or left side of the face according to the randomization scheme. The opposite side of the face remained untreated. Treatment was randomized between the right and left side of the face for odd and even-numbered subjects. The randomization scheme showed which treatment was assigned to each side of the face.

Prior to any application at the testing facility on Day 0 (baseline), the following procedures will be followed in the AM:

Baseline Photographs (VISIA CR® IMAGING SYSTEM) PHOTO #1
Baseline Subject Questionnaire
Baseline Global Assessment By A Trained Evaluator Products were then applied according to the following procedure:

A.M. Treatment

1. A pea-sized amount of NU DERM Gentle Cleanser is dispensed, rubbed on wet hands and applied to full face and cleansed thoroughly, and rinsed with tepid water with technician supervision.

2. Post-wash photographs (VISIA CR® Imaging System) were taken immediately following wash.

3. Two pumps (approximately 1 ml) of the anti-redness composition of Example 4 were applied to one side of the face as instructed.

4. Two pumps (approximately 1 ml) of the protective composition of Example 3 were applied to one side of the face as instructed.

5. Immediately following application of previous two products, another photo was taken.

6. After waiting 10-30 minutes to determine when erythema subsided, another photo was taken.

7. A trained evaluator made an assessment of tolerability of the treatment.

P.M. Treatment at Home Prior to Bedtime

1. A pea-sized amount of NU DERM Gentle Cleanser is dispensed, rubbed on wet hands and applied to full face and cleansed thoroughly, and rinsed with tepid water.

2. 0.5 mL of Metronidazole (0.5 mL syringe delivery) was applied to one side of the face as instructed.

3. Two pumps (approximately 1 ml) of the anti-redness composition of Example 4 were applied to one side of the face as instructed.

Metronidazole was supplied to the subjects in pre-filled syringes at each scheduled visit, and each syringe delivered 0.5 mL of product (Metronidazole Topical Gel).

After applications, the subjects were given their assigned product with use instructions and a daily diary to record their daily usage and any safety related comments they may have. Subjects were also be given a questionnaire to be completed following their PM application just prior to bedtime. Subjects returned all completed questionnaires at the next scheduled visit. Photographs will be taken at the following time points at the Day 0 (baseline visit).

Baseline (photo #1)
Immediately post-wash (photo #2)
Post-treatment of both product applications (photo #3)
10-30 minutes post-treatment (photo #4)

Photographs were taken immediately post-wash and post-application of products at all other visits.

The subjects avoided any other medicated formulations on the face (including cleansers), and used only the products supplied to them during the study. Subjects were instructed not introduce any new facial cosmetics, soaps, shampoos, creams, lotions, etc. while on this study. Subjects were permitted to use their daily cosmetics (lipstick, eye makeup, foundation) during the study. However, subjects presented themselves to the clinic with nothing applied to their face at scheduled visits.

Irritation Evaluation

A trained evaluator assessed (global assessment) the right and left side of the face of each subject at all visits. The Board-Certified Dermatologist conducted the global tolerability assessments pre- and post-application of the test regimen on the final day of the study. Tolerability assessments were conducted according to the scales below.

Scale for Scoring Redness/Irritation
0=No irritation present
1-3=Mild irritation present
4-6=Moderate irritation present
7-9=Severe irritation present

| Scale for Sensory Evaluation | |
|---|---|
| (stinging [S]), burning [B]) | (itching [I]) |
| 0 = None—no stinging/burning | 0 = No itching |
| 1-3 = Mild—light warm, tingling sensation, not really bothersome | 1-3 = Mild—occasional, slight itching |
| 4-6 = Moderate—definite warmth, tingling sensation, that is somewhat bothersome | 4-6 = Moderate—constant or intermittent itching that is somewhat bothersome |
| 7-9 = Severe—hot tingling sensation which is disturbing normal activity | 7-9 = Severe—bothersome itching which is disturbing normal activity |

Photographic images taken using the VISIA CR® (Canfield Scientific) will be analyzed using Image PRO® software to determine changes (if any) in the a* value (white to red). An increase in the a* value indicates an increase in erythema.

All data points collected after Days 0-4, 11, 18, and 25 were compared to the baseline for each subject for differences between the time points and control. The average results for all subjects of the post-wash comparisons are presented in Table F. The data in Table F shows that at day zero, the negative 0.71 value indicates that the untreated side of face in study was redder initially than the side of the face that was not part of the study. This is simply a result of the randomness of the study. Between day 0 and day 4, the treated side of the face became the less red side as a result of the treatment.

TABLE F

| Day | a* values |
|---|---|
| 1 | -0.71 |
| 4 | .14 |
| 11 | .36 |
| 18 | .25 |
| 25 | .61 |

The summation of the difference was analyzed using the Wilcoxon Signed-Rank Test. A response was considered statistically significantly different from baseline when the p-value is <0.05.

The tested regimen resulted in a marked reduction in redness. As shown in Table F, after washing, the redness of the treated side was reduced significantly compared to the control side of the face. This reduction was greater than the redness reduction expected from Metrogel alone, especially since the clinical application for Metrogel is resolution of lesions, not the reduction of redness.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments.

What is claimed is:

1. A method of promoting vasoconstriction of an area of skin afflicted with rosacea, consisting essentially of:
    cleansing the area of skin afflicted with rosacea;
    applying a redness reducing amount of a composition containing a Cu/Zn malonate complex to the afflicted area;
    applying a composition containing metronidazole to the afflicted area;
    applying a protective composition to the afflicted area that has been cleansed and treated with the composition containing the Cu/Zn malonate complex and the composition containing metronidazole, which protective composition optionally further includes a sunscreen;
    wherein the composition containing the Cu/Zn malonate complex optionally further includes a moisturizer, and the cleansing step optionally includes cleaning the area of skin afflicted with rosacea with an antimicrobial cleanser, and
    wherein the method optionally further consists essentially of applying an anti-parasitic product and/or an anti-acne medication to the area of skin afflicted with rosacea after the protective composition is applied,
    thereby promoting vasoconstriction of the area of skin afflicted with rosacea.

2. The method of claim 1, wherein the antimicrobial cleanser is selected from the group consisting of chlorhexidine gluconate, triclosan, zinc pyrithione, clindamycin phosphate, sodium sulphacetamide and combinations thereof.

3. The method of claim 1, wherein the sunscreen comprises a compound selected from the group consisting of ZnO, Vitamin A, Vitamin D and combinations thereof.

4. The method of claim 1, wherein the anti-parasitic product includes a compound selected from the group consisting of benzyl benzoate, salicylic acid and combinations thereof.

5. The method of claim 1, wherein the anti-acne medication is selected from the group consisting of benzoyl peroxide, retinoids, tetracycline, clindamycin, erythromycin, and combinations thereof.

6. The method of claim 1, wherein the composition containing metronidazole is formulated as a gel preparation.

7. The method of claim 1, wherein the composition containing metronidazole contains from 0.001% to 5% metronidazole by weight of the composition.

* * * * *